(12) United States Patent
Geschwind et al.

(10) Patent No.: US 9,737,487 B2
(45) Date of Patent: Aug. 22, 2017

(54) CYCLODEXTRIN COMPOSITIONS ENCAPSULATING A SELECTIVE ATP INHIBITOR AND USES THEREOF

(71) Applicant: The Johns Hopkins University, Baltimore, MD (US)

(72) Inventors: Jean-Francois Geschwind, Potomac, MD (US); Shanmugasundaram Ganapathy-Kanniappan, Baltimore, MD (US); Surojit Sur, Gaithersburg, MD (US); Bert Vogelstein, Baltimore, MD (US); Kenneth W. Kinzler, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 14/643,603

(22) Filed: Mar. 10, 2015

(65) Prior Publication Data
US 2016/0015639 A1    Jan. 21, 2016

Related U.S. Application Data

(63) Continuation of application No. PCT/US2015/011344, filed on Jan. 14, 2015.

(60) Provisional application No. 61/992,572, filed on May 13, 2014, provisional application No. 61/927,259, filed on Jan. 14, 2014.

(51) Int. Cl.
| | |
|---|---|
| *A61K 47/40* | (2006.01) |
| *A61K 9/14* | (2006.01) |
| *A61K 31/02* | (2006.01) |
| *A61K 31/19* | (2006.01) |
| *A61K 45/06* | (2006.01) |
| *A61K 9/08* | (2006.01) |
| *A61K 47/48* | (2006.01) |
| *C08B 37/16* | (2006.01) |
| *C08L 5/16* | (2006.01) |
| *A61K 9/19* | (2006.01) |

(52) U.S. Cl.
CPC ............ *A61K 9/146* (2013.01); *A61K 9/08* (2013.01); *A61K 31/02* (2013.01); *A61K 31/19* (2013.01); *A61K 45/06* (2013.01); *A61K 47/40* (2013.01); *A61K 47/48969* (2013.01); *C08B 37/0012* (2013.01); *C08B 37/0015* (2013.01); *C08L 5/16* (2013.01); *A61K 9/19* (2013.01)

(58) Field of Classification Search
None
See application file for complete search history.

(56) References Cited

U.S. PATENT DOCUMENTS

| | | |
|---|---|---|
| 4,337,760 A | 7/1982 | Rubin |
| 4,536,387 A | 8/1985 | Sakamoto et al. |
| 5,213,804 A | 5/1993 | Martin et al. |
| 5,759,547 A | 6/1998 | Maione |
| 5,759,837 A | 6/1998 | Kuhajda et al. |
| 5,854,067 A | 12/1998 | Newgard et al. |
| 6,284,786 B1 | 9/2001 | Casciari et al. |
| 6,312,662 B1 | 11/2001 | Erion et al. |
| 6,448,030 B1 | 9/2002 | Rust et al. |
| 6,670,330 B1 | 12/2003 | Lampidis et al. |
| 7,547,673 B2 | 6/2009 | Ko et al. |
| 8,119,116 B2 | 2/2012 | Ko et al. |
| 2001/0046997 A1 | 11/2001 | Abraham et al. |
| 2002/0006915 A1 | 1/2002 | Mack Strong et al. |
| 2002/0068711 A1 | 6/2002 | Pedersen et al. |
| 2003/0018166 A1 | 1/2003 | Sacchettini et al. |
| 2003/0087961 A1* | 5/2003 | Ko .................... A61K 31/19 514/557 |
| 2003/0139331 A1 | 7/2003 | Martin et al. |
| 2004/0029826 A1 | 2/2004 | Sokoloff et al. |
| 2004/0167079 A1 | 8/2004 | Tidmarsh |
| 2004/0167196 A1 | 8/2004 | Tidmarsh |
| 2006/0058383 A1* | 3/2006 | Huang .................. A61K 31/22 514/546 |
| 2006/0154867 A1 | 7/2006 | Sokoloff et al. |
| 2010/0330197 A1 | 12/2010 | Higashiguchi et al. |

FOREIGN PATENT DOCUMENTS

| | | |
|---|---|---|
| WO | WO-97/04104 A2 | 2/1997 |
| WO | WO-2006/010073 | 1/2006 |
| WO | WO-2007/097989 | 8/2007 |
| WO | WO-2014/004651 A1 | 1/2014 |

OTHER PUBLICATIONS

LookChem, Bromopyruvic acid, http://www.lookchem.com/Bromopyruvic-acid/, retrieved online on Feb. 2, 2016.*
Moses, Beta Cyclodextrin—Insulin-Encapsulated Chitosan/Alginate Matrix: Oral Delivery System, 1991.*
Vyas, Cyclodextrin based novel drug delivery systems, J Incl Phenom Macrocycl Chem (2008) 62:23-42.*
Singh et al, Reduced Toxicity and Enhanced Antitumor Efficacy of Betacyclodextrin Plumbagin Inclusion Complex in Mice Bearing Ehrich Ascites Carcinoma, Indian J Physiol Pharmacol 1997; 41(2): 171-175.*
Ando, et al., "Hepatic Arterial Infusion Chemotherapy for Advanced Hepatocellular Carcinoma with Portal Vein Tumor Thrombosis," Cancer, 95: 588-595 (2002).
Archived webpage from Touch Oncology; https://web.archive.org/web/20070211104624/https://www.touchoncologicaldisease.com/articles.cfm?article_id=6103&level=2.
Cohen and Kemeny, "An Update on Hepatic Arterial Infusion Chemotherapy for Colorectal Cancer," The Oncologist, 8: 553-556 (2003).
Declaration dated Sep. 15, 2016 by Dr. Harrie Verhoeven. (Cited in Opposition of European Patent No. 2 331 092 B1, filed on Dec. 18, 2014.).

(Continued)

*Primary Examiner* — Jennifer A Berrios
(74) *Attorney, Agent, or Firm* — Foley Hoag LLP

(57) ABSTRACT

The invention provides compositions comprising cyclodextrins encapsulating a selective ATP inhibitor, as well as uses thereof.

27 Claims, 15 Drawing Sheets

(56) References Cited

OTHER PUBLICATIONS

Declaration dated Sep. 15, 2016 by Dr. Young Ko. (Cited in Opposition of European Patent No. 2 331 092 B1, filed on Dec. 18, 2014.).
Email #2, reply from Dr. Young Ko to Dr. Harrie Verhoeven on Oct. 7, 2008. (Cited in Opposition of European Patent No. 2 331 092 B1, filed on Dec. 18, 2014.).
Email #3, reply from Dr. Harrie Herhoeven to Dr. Young Ko on Oct. 7, 2008. (Cited in Opposition of European Patent No. 2 331 092 B1, filed on Dec. 18, 2014.).
Geschwind, et al., "Effects of intraarterial delivery of 3-bromopyruvate on tumor apoptosis: Comparison between 1 hr. infusion and serial bolus injections in an animal model of liver cancer," American Society of Clinical Oncology, Gastrointestinal Cancers Symposium, Abstract No. 216 (2006).
Geschwind, et al., "Recently elucidated energy catabolism pathways provide opportunities for novel treatments in hepatocellular carcinoma," Expert Rev Anticancer Ther, 4(3): 449-457 (2004).
Grosse et al., "In Vitro Modulation of Doxorubicin and Docetaxel Antitumoral Activity by Methyl-Beta-cyclodextrin," Eur J Cancer, 34(1): 168-174 (1998).
Hamada et al., "Enhancement of Water-Solubility and Bioactivity of Paclitaxel Using Modified Cyclodextrins," J Biosci Bioeng, 102(4): 369-371 (2006).
Ko, et al., "A translational study "case report" on the small molecule "energy blocker" 3-bromopyruvate (3BP) as a potent anticancer agent: from bench side to bedside," J Bioenerg Biomembr, 44: 163-170 (2012).
Liapi and Geschwind, "Transcatheter Arterial Chemoembolisation (TACE) for HCC—Classic Concepts and Future Evolution," European Oncological Disease, 1(1): 47-52 (2006).
NIH Grant Award No. 1 R01CA100883-A0, submitted 202 (redacted). Project title: "Therapy for Liver Cancer by Targetting Energy Metabolism," Principle Investigator: JF Geschwind.
NIH Grant Award No. 5 R01CA100883-02, Issue Date Mar. 30, 2006. Project title: "Therapy for Liver Cancer by Targeting Energy Metabolism," Principle Investigator: JF Geschwind.
Okamatsu et al., "Folate-Appended Beta-Cyclodextrin as a Promising Tumor Targeting Carrier for Antitumor Drugs in Vitro and in Vivo," Bioconjugate Chem, 24: 724-733 (2013).
Vali et al., "Effects of Intraarterial Delivery of 3-Bromopyruvate on Tumor Apoptosis: Comparison of 1Hr Infusion to Serial Bolus Injections in an Animal Model of Liver Cancer," Radiological Society of North America (RSNA), Scientific Assembly and Annual Meeting, (2005).
Zhang, et al., "Aerosolized 3-Bromopyruvate inhibits lung tumorigenesis without causing liver toxicity," Cancer Prev Res, 5(5): 717-725 (2012).
U.S. Appl. No. 61/090,793, Geschwind.
U.S. Appl. No. 61/097,408, Geschwind.
U.S. Appl. No. 61/165,239, Geschwind.
Arafat et al., "Toxicities Related to intraarterial Infusion of Cisplatin and Etoposide in Patients with Brain Tumors," J. of Neuro-oncology, 42:73-77 (1999).
Bar et al., "Sorbitol Removal by the Metastatic Liver: A Predictor of Systemic Toxicity of Intra-arterial Chemotherapy in Patients with Liver Metastases," J. of Hepatology, 30:1112-1118 (1999).
Chen et al., "The Warburg effect and its cancer therapeutic implications," J Bioenerg Biomembr, 39: 267-274 (2007). (Cited in Opposition of European Patent No. 09808532.7, filed on Jan. 8, 2016.).
Chang et al., "Local Toxicity of Hepatic Arterial Infusion of Hexokinase II Inhibitor, 3-Bromopyruvate: In Vivo Investigation in Normal Rabbit Model". Academic Radiology, 14(1):85-92 (2007). (Cited in Opposition of European Patent No. 2 331 092 B1, filed on Dec. 18, 2014.).
Costello et al., "Evidence for Changed in RREB-1, ZIP3, and Zinc in the Early Development of Pancreatic Adenocarcinoma," J Gastrointest Canc, 43: 570-578 (2012).

Cover e-mail from Dr. X to Dr. Y enclosing attachments and attachments (Feb. 10, 2009). (Cited in Opposition of European Patent No. 2 331 092 B1, filed on Dec. 18, 2014.).
Curriculum vitae of Professor Margarida Casal. (Cited in Opposition of European Patent No. 09808532.7, filed on Jan. 8, 2016.).
Curriculum vitae of Professor Stanislaw Ulaszewski. (Cited in Opposition of European Patent No. 09808532.7, filed on Jan. 8, 2016.).
Declaration dated Dec. 14, 2015 by Professor Stanislaw Ulaszewski, University of Wroclaw, Poland. (Cited in Opposition of European Patent No. 09808532.7, filed on Jan. 8, 2016.).
Declaration dated Dec. 17, 2015 by Professor Margarida Casal, University of Minho, Portugal. (Cited in Opposition of European Patent No. 09808532.7, filed on Jan. 8, 2016.).
Deposition of Dr. Geschwind on Mar. 21, 2006, in *Ko v. The Johns Hopkins University, et al.*, 05-CV-1475-WDQ (2005), in the US District Court for the District of Maryland (selected pages). (Cited in Opposition of European Patent No. 09808532.7, filed on Jan. 8, 2016.).
DiFeo, "Drug Product Development: A Technical Review of Chemistry, Manufacturing, and Controls Information for the Support of Pharmaceutical and Compound Licensing Activities", Drug Dev Industrial Pharm 29(9):939-958 (2003). (Cited in Opposition of European Patent No. 2 331 092 B1, filed on Dec. 18, 2014.).
Email #1 entitled "BrPyruvate HCC" from Dr. X to Dr. Y (names redacted) (Oct. 7, 2008). (Cited in Opposition of European Patent No. 2 331 092 B1, filed on Dec. 18, 2014.).
Email #2: Reply to Email #1 from Dr. Y to Dr. X (Oct. 7, 2008). (Cited in Opposition of European Patent No. 2 331 092 B1, filed on Dec. 18, 2014.).
Email from the American Board of Radiology (ABR) to the Opponent, dated Mar. 25, 2015. (Cited in Opposition of European Patent No. 09808532.7, filed on Jan. 8, 2016.).
Ethical Approval Letter from Prof. Dr. Med. Sebastian Harder to Prof. Dr. Thomas Vogl (Feb. 23, 2009). (Cited in Opposition of European Patent No. 2 331 092 B1, filed on Dec. 18, 2014.).
Fiebig et al., "Relevance of Tumor Models for Anticancer Drug Development," Contrib. Oncol. Basel. Karger, 54:109-120 (1999).
Geschwind et al., "Novel Therapy for Liver Cancer: Direct Intraarterial Injection of a Potent Inhibitor of ATP Production," Cancer Research, 62:3909-3913 (2002).
Glick et al., "The antitumor agent 3-bromopyruvate has a short half-life at physiological conditions," Biochem Bioph Res Co. 452(1): 170-173 (2014). (Cited in Opposition of European Patent No. 09808532.7, filed on Jan. 8, 2016.).
Gobin et al., "Intraarterial Chemotherapy for Brain Tumors by Using a Spatial Dose Fractionation Algorithm and Pulsatile Delivery," Radiology, 218(3):724-732 (2001).
Godin et al., "Repeat Dose Toxicity Studies of 3-Brorhopyruvate in Rats Following Oral and Intraperitoneal Administration". American College of Toxicology, 34th Annual Meeting Program, San Antonio, Texas, Abstract P304, Nov. 3-6, 2013. (Cited in Opposition of European Patent No. 2 331 092 B1.).
Higashi, T. et al., "Relationship Between Retention Index in Dual-Phase 18F-FDG PET, and Hexokinase-II and Glucose Transporter-1 Expression in Pancreatic Cancer," J Nucl Med, 43:173-180 (2002).
International Search Report dated Jun. 3, 2008 from PCT/US2007/087740.
International Search Report dated May 3, 2010 from PCT/US2009/004789.
International Search Report dated Jul. 2, 2015 from PCT/US2015/011344.
Johns Hopkins Medical Institutions Office of Communications and Public Affairs "Energy Blocker May Be Potential Liver Cancer Treatment," www.hopkinsmedicine.org/press/2002/July020715.htm.
Kerr et al., "Phase I Clinical and Pharmacokinetic Study of Leucovorin and Infusional Hepatic Arterial Flurouracil," J. of Clinical Oncology, 13(12):2968-2972 (1995).
Kerr et. al., "Phase I clinical and pharmacokinetic study of leucovorin and infusional hepatic arterial fluorouracil," Chemical Abstracts, 124:193528 (1995).

(56) References Cited

OTHER PUBLICATIONS

Kim et al. "Apoptosis-inducing Antitumor Efficacy of Hexokinase II inhibitor in Hepatocellular Carcinoma", Mol Cancer Ther, 6(9):2554-62 (2007). (Cited in Opposition of European Patent No. 2 331 092 B1, filed on Dec. 18, 2014.).
Ko et al., "Advanced Cancers: Eradication in All Cases Using 3-bromopyruvate Therapy to Deplete ATP," Biochem Biophys Res Commun, 324(1):269-275 (2004).
Ko et al., "Advanced Cancers: Eradication in All Cases Using 3-bromopyruvate Therapy to Deplete ATP," Press Release, Nov. 5, 2004.
Ko et al., "Glucose catabolism in the Rabbit VX2 Tumor Model for Liver Cancer: Characterization and Targeting Hexokinase," Cancer Letters, 173:83-91 (2001).
Ko et al., "Metabolic Properties of the Rabbit VX2 Tumor Model Following Liver Implantation: Role for Hexokinase," Cancer Research, 42:519 (2001).
Kostron et Si., "Photodynamic Treatment of Malignant Brain Tumors," Jg 102, Heft 18:531-535 (1990).
Letter from Professor Stanislaw Ulazewski, Institute of Genetics and Microbiology, University of Wraclaw, Poland. (Dec. 18, 2014). (Cited in Opposition of European Patent No. 2 331 092 B1.).
Lin et al., "Effects of 90Y-Microspheres on Liver Tumors: Comparison of Intratumoral Injection Method and Intra-Arterial Injection Method," The J. of Nuclear Medicine, 41(11):1892 (2000).
Maryland Board of Physicians Practitioner Profile of Dr Geschwind, dated Aug. 5, 2015. (Cited in Opposition of European Patent No. 09808532.7, filed on Jan. 8, 2016.).
Material Safety Data Sheet for Idarubicin hydrochloride (Bedford Laboratories) (Dec. 10, 2005). (Cited in Opposition of European Patent No. 2 331 092 B1, filed on Dec. 18, 2014.).
Material Safety Data Sheet for Idarubicin hydrochloride (Teva Sicor) (Aug. 3, 2007). (Cited in Opposition of European Patent No. 2 331 092 B1, filed on Dec. 18, 2014.).
Mathupala et al., "Glucose Catabolism in Cancer Cells," The J. of Biological Chemistry, 276(46):43407-43412 (2001).
Miccoli, L. et al., "Intracellular pH Governs the Subcellular Distribution of Hexokinase in a Glioma Cell Line," Biochem. J., 313:957-962 (1996).
Minn, H. et al., "Determination of 2-fluoro-2-deoxy-D-Glucose Uptake and ATP Level for Evaluating Drug Effects in Neoplastic Cells," Res Exp Med, 191:27-35 (1991).
National Cancer Institute (NCI) in vivo cancer screen data L1210, Leukemia (intraperitoneal) in B6D2F1 (DBF1) mice. (Cited in Opposition of European Patent No. 2 331 092 B1, filed on Dec. 18, 2014.).
Nelson, K. et al., "3-Bromopyruvate Kills Cancer Cells in Animals," The Lancet Oncology, 3(9):524 (2002) Abstract Only.
NIH Grant Award R01 CA100803-01A2 to Dr. Geschwind, Mar. 10, 2005 (selected pages). (Cited in Opposition of European Patent No. 09808532.7, filed on Jan. 8, 2016.).
Office Action Issued in U.S. Appl. No. 10/243,350 dated Dec. 16, 2004.
Office Action issued in U.S. Appl. No. 10/243,550 dated Jul. 1, 2005.
Office Action Issued in U.S. Appl. No. 10/243,550 dated Feb. 10, 2006.
Office Action Issued in U.S. Appl. No. 10/243,550 dated Nov. 30, 2006.
Office Action Issued in U.S. Appl. No. 10/243,550 dated Aug. 21, 2007.
Office Action Issued in U.S. Appl. No. 10/243,550 dated Jun. 24, 2008.
Office Action Issued in U.S. Appl. No. 10/243,550 dated Oct. 3, 2008.
Pedersen et al., "Mitochondrial Bound Type II Hexokinase: a Key Player in the Growth and Survival of Many Cancers and an Ideal Prospect for Therapeutic Intervention," Biochimica and Biophysics Acta, 1555:14-20 (2002).
Pedersen, P., ""Energy Blocker" Kills Big Tumors in Rats," Audio File—Johns Hopkins Medicine, Office of Corporate Communications, Oct. 14, 2004.
Reply to Email #2 from Dr. X to Dr, Y (Oct. 7, 2008). (Cited in Opposition of European Patent No. 2 331 092 B1, filed on Dec. 18, 2014.).
Rothbarth et al., "Melphalan Antitumor Efficacy and Hepatotoxicity: The Effect of Variable Infusion Duration in the Hepatic Artery," The Journal of Pharmacology and Experimental Therapeutics, 305(3)1098-1103 (2003).
Shin, S.W. et al., "Hepatic Intra-Arterial Injection of 3-bromopyruvate in Rabbit VX2 Tumor," Acta Radiologica, 47(10):1036-1041 (2006).
Soulen et al., "Intraarterial Chemotherapy with Limb-sparing Resection of Large Soft-tissue Sarcomas of the Extremities " JVIR, 3:659-663 (1992).
Sporn et al., "Chemoprevention of Cancer," Carcinogenesis, 21(3): 525-530 (2000).
Sprinson et al., "A study of β-hydroxy-α-keto acids," J Biol Chem, 164: 417-32 (1946). (Cited in Opposition of European Patent No. 09808532.7, filed on Jan. 8, 2016.).
Supplementary European Search Report dated Aug. 30, 2011 from EP 09 80 8532.
Supplementary European Search Report for EP 07 86 9361 dated Jul. 26, 2011.
USPC Entry on Idarubicin hydrochloride (Jan. 4, 2002). (Cited in Opposition of European Patent No. 2 331 092 B1, filed on Dec. 18, 2014.).
Vali et al., "Intraarterial Therapy with a New Potent Inhibitor of Tumor Metabolism (3-bromopyruvate): Identification of Therapeutic Dose and Method of Injection in an Animal Model of Liver Cancer," Journal of Vascular and Interventinal Radiology, 18(1):95-101 (2007).
Vali et al., "Targeting of VX2 Rabbit Liver Tumor by Selective Delivery of 3-Bromopyruvate: A Biodistribution and Survival Study", J Pharmacol Exp Ther, 327(1):32-37. (Cited in Opposition of European Patent No. 2 331 092 B1, filed on Dec. 18, 2014.).
Vossen et al., "Development of a new orthotopic animal model of metastatic liver cancer in the rabbit VX2 model: effect on metastases after partial hepatectomy, intra-arterial treatment with 3-bromopyruvate and chemoembolization," Clin Exp Metastasis 25(7):811-817 (2008).
Wang et al, "Isolated Lower Extremity Chemotherapeutic Infusion for Treatment of Osteosarcoma: Experimental Study and Preliminary Clinical Report," J. Vasc. Interv. Radiol., 12:731-737 (2001).
Xu et al., "inhibition of Glycolysis in Cancer Cells: a Novel Strategy to Overcome Drug Resistance Associated with Mitochondrial Respiratory Defect and Hypoxia," Cancer Res, 65(2): 613-621 (2005). (Cited in Opposition of European Patent No. 09808532.7, filed on Jan. 8, 2016.).
Yamada, K. et al., "Factors Influencing [F-18] 2-Fluoro-2-Deoxy-D-Glucose (F-18 FDG) Uptake in Melanoma Cells: The Role of Proliferation Rate, Viability, Glucose Transporter Expression and Hexokinase Activity," The J. of Dermatology, 32:316-334 (2005).
Yates et al., "Activation of insulin-secreting cells by pyruvate and halogenated derivatives," Biochm. J., 265:283-287 (1990).
Yun et al., "Spectrophotometric determination of bromopyruvate by reaction with 2-nitro-5-thiobenzoic acid," Anal Biochem, 85(2): 437-441 (1978). (Cited in Opposition of European Patent No. 09808532.7, filed on Jan. 8, 2016.).

* cited by examiner

A

B

A Matrigel Invasion Assay Suit-2

B Matrigel Invasion Assay MiaPaCa-2

C MMP-9 Activity in Zymography

D MMP-9 Secretion in Western Blot

CYCLODEXTRIN COMPOSITIONS ENCAPSULATING A SELECTIVE ATP INHIBITOR AND USES THEREOF

RELATED APPLICATIONS

This application is a continuation of International Application No. PCT/US2015/011344, filed on Jan. 14, 2015, which claims the benefit of U.S. Provisional Application No. 61/927,259, filed on Jan. 14, 2014, and U.S. Provisional Application No. 61/992,572, filed on May 13, 2014; which are hereby incorporated by reference.

STATEMENT OF RIGHTS

This invention was made with government support under Grant Numbers R01 CA160771, P30 CA006973, and NCRR UL1 RR 025005 awarded by the National Institutes of Health. The U.S. government has certain rights in the invention. This statement is included solely to comply with 37 C.F.R. §401.14(a)(f)(4) and should not be taken as an assertion or admission that the application discloses and/or claims only one invention.

BACKGROUND OF THE INVENTION

The knowledge that cancer cells rely on increased glycolysis rather than oxidative phosphorylation for survival is known as the "Warburg hypothesis" (Warburg (1956) *Science* 123:309-314). This concept constitutes the basis for using glycolysis and its associated enzymes as unique targets for the development of new anticancer therapeutic agents (Shaw (2006) *Curr. Opin. Cell Biol.* 18:598-608; Gatenby and Gillies (2007) *Biochem. Cell Biol.* 39:1358-1366). One such agent is 3-bromopyruvate (3-BrPA), a synthetic brominated derivative of pyruvic acid that acts as an irreversible glycolytic inhibitor (Ko et al. (2001) *Cancer Lett.* 173:83-91; Geschwind et al. (2002) *Cancer Res.* 62:3909-3913). It disrupts energy metabolism by targeting the glycolytic enzyme, glyceradehyde-3 phosphate dehydrogenase (GAPDH) (Ganapathy-Kanniappan et al. (2009) *Anticancer Res.* 29:4909-4918). Further, the anticancer effects of 3-BrPA have been consistent and reproducible against multiple tumor models both in vitro and in vivo. A wide variety of tumors have been demonstrated to be sensitive to 3-BrPA treatment, including, for example, liver cancer (Geschwind et al. (2002) *Cancer Res.* 62:3909-30913; Vali et al. (2007) *J. Vasc. Interv. Radiol.* 18:95-101; and Ganapathy-Kanniappan et al. (2012) *Radiology* 262:834-845), pancreatic cancer (Cao et al. (2008) *Clin. Cancer Res.* 14:1831-1839; Bhardwaj et al. (2010) *Anticancer Res.* 30:743-749; and Ota et al. (2013) *Target Oncol.* 8:145-151), brain tumor (El Sayed et al. (2012) *J. Bioenerg. Biomembr.* 44:61-79; Davidescu et al. (2012) *J. Bioenerg. Biomembr.* 44:51-60) and breast cancer (Buijs et al. (2013) *J. Vasc. Interv. Radiol.* 24:737-743). Together, the inhibition of GAPDH and the molecular specificity of 3-BrPA have established that targeting tumor glycolysis via 3-BrPA could be a viable strategy in treating cancer, especially solid malignancies (Ganapathy-Kanniappan et al. (2012) *Oncotarget* 3:940-95; Ganapathy-Kanniappan et al. (2013) *Anticancer Res.* 33:13-20).

Despite the potential of selective ATP inhibitors, such as 3-halopyruvates like 3-BrPA, for therapeutic use, however, there are several factors that have hampered development of systemic administration formulations. For example, the alkylation (chemical) properties of 3-halopyruvates and related compounds render them very reactive with electrophilic molecules that has generally required increases in dosing with the negative effect of increasing toxicity, especially increased alkylation near the injection site. In particular, the presence of water or any nucleophilic group, such as amino or sulfhydryl groups commonly found in proteins, chemically inactivates the compound. Also, the in vivo stability of such compounds is influenced by multiple factors including glutathione, NADH and other reducing molecules in the blood and circulatory system. Hence, it is critical that the compounds remain unaffected by such factors, at least until the first pass of circulation.

While recognizing that protecting selective ATP inhibitors, such as 3-halopyruvates like 3-BrPA, until they are delivered to organs or tissues is critical for their antitumor efficacy under systemic delivery, numerous approaches to achieve such protection, such as encapsulating them in liposomes, microspheres, nanospheres, nanoparticles, bubbles, and the like, have not been successful. For example, it is known that molecules such as 3-BrPA undesirably leach out rapidly from PEGylated liposomes or react with proteins such as albumin in albumin-based nanoparticles. Although sporadic reports have documented the intraperitoneal delivery of 3-BrPA in preclinical models, the efficacy and dosage regimen were very limited. Due to these failures, 3-BrPA therapies are currently relegated to locoregional delivery (e.g., percutaneous ablation, intra-arterial delivery, and intra-tumoral injections) as opposed to systemic delivery (Kunjithapatham et al. (2013) *BMC Res. Notes* 6:277).

Accordingly, there is a great need in the art to identify compositions of selective ATP inhibitors, such as 3-halopyruvates like 3-BrPA, suitable for systemic administration.

SUMMARY OF THE INVENTION

The present invention is based in part on the discovery that encapsulating selective inhibitors of ATP production, such as 3-halopyruvates (e.g., 3-BrPA), within cyclodextrins both a) stabilizes the alkylating agent in vivo by protecting the halogen moiety away from aqueous and nucleophilic environments that would deactivate the compound and b) provides a steady release of the compound necessary to maintain a reasonable half-life of the compound in vivo.

In one aspect, a composition comprising a cyclodextrin and a pharmaceutical agent represented in the general formula:

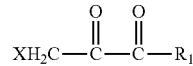

wherein, independently of each occurrence: X represents a halide, a sulfonate, a carboxylate, an alkoxide, or an amine oxide; $R_1$ represents OR, H, N(R")$_2$, C1-C6 alkyl, C6-C12 aryl, C1-C6 heteroalkyl, or C6-C12 heteroaryl; R" represents H, C1-C6 alkyl, or C6-C12 aryl; R represents H, alkali metal, C1-C6 alkyl, C6-C12 aryl or C(O)R'; and R' represents H, C1-C20 alkyl or C6-C12 aryl, wherein the cyclodextrin encapsulates the pharmaceutical agent, is provided. In one embodiment, at least one α-D-glucopyranoside unit of the cyclodextrin has at least one hydroxyl chemical group replaced with an ionizable chemical group. In another embodiment, the at least one hydroxyl chemical group of the at least one α-D-glucopyranoside unit is selected from the group consisting of C2, C3, and C6 hydroxyl chemical groups. In still another embodiment, the C2, C3, and C6 hydroxyl chemical groups of at least one α-D-glucopyranoside unit of the cyclodextrin that are replaced with ionizable chemical groups. In yet another embodiment, the at least one α-D-glucopyranoside unit of the cyclodextrin is selected from the group consisting of two, three, four, five, six, seven, eight, and all α-D-glucopyranoside units of the cyclodextrin. In another embodiment, the ionizable chemical group is the same at all replaced positions. In still another embodiment, the ionizable chemical group is a weakly basic functional group or a weakly acidic functional group. For example, the weakly basic functional group (X) can have a $pK_a$ between 6.5 and 8.5 according to $CH3-X^-$ or the weakly acidic functional group (Y) can have a $pK_a$ between 4.0 and 6.5 according to $CH_3-Y$. In yet another embodiment, the weakly basic or weakly acidic functional groups are selected from the group consisting of amino, ethylene diamino, dimethyl ethylene diamino, dimethyl anilino, dimethyl naphthylamino, succinyl, carboxyl, sulfonyl, and sulphate functional groups. In another embodiment, the cyclodextrin has a $pK_{a1}$ of between 4.0 and 8.5. In still another embodiment, the composition is a liquid or solid pharmaceutical formulation. In yet another embodiment, the pharmaceutical agent is neutrally charged or hydrophobic. In another embodiment, the cyclodextrin is selected from the group consisting of β-cyclodextrin, α-cyclodextrin, and γ-cyclodextrin. In still another embodiment, the cyclodextrin is β-cyclodextrin. In yet another embodiment, the pharmaceutical agent is 3-halopyruvate. In another embodiment, the pharmaceutical agent is 3-bromopyruvate. In still another embodiment, the composition is formulated for systemic administration. In yet another embodiment, the composition further comprises an anti-cancer therapeutic agent.

In another aspect, a kit comprising a composition described herein, and instructions for use, is provided.

In still another aspect, a method of treating a subject having a cancer comprising administering to the subject a therapeutically effective amount of a composition described herein, is provided. In one embodiment, the composition is administered systemically. In another embodiment, the systemic administration is selected from the group consisting of oral, intravenous, intraperitoneal, subcutaneous, and intramuscular administration. In still another embodiment, the subject is treated with at least one additional anti-cancer therapy. In yet another embodiment, the at least one additional anti-cancer therapy is radiation therapy. In another embodiment, the cancer is a solid tumor. In still another embodiment, the cancer is selected from the group consisting of liver cancer, pancreatic cancer, lung cancer and breast cancer. In yet another embodiment, the cancer is liver cancer. In another embodiment, the subject is a mammal. In still another embodiment, the mammal is a human.

DETAILED DESCRIPTION OF THE INVENTION

Figure 1:
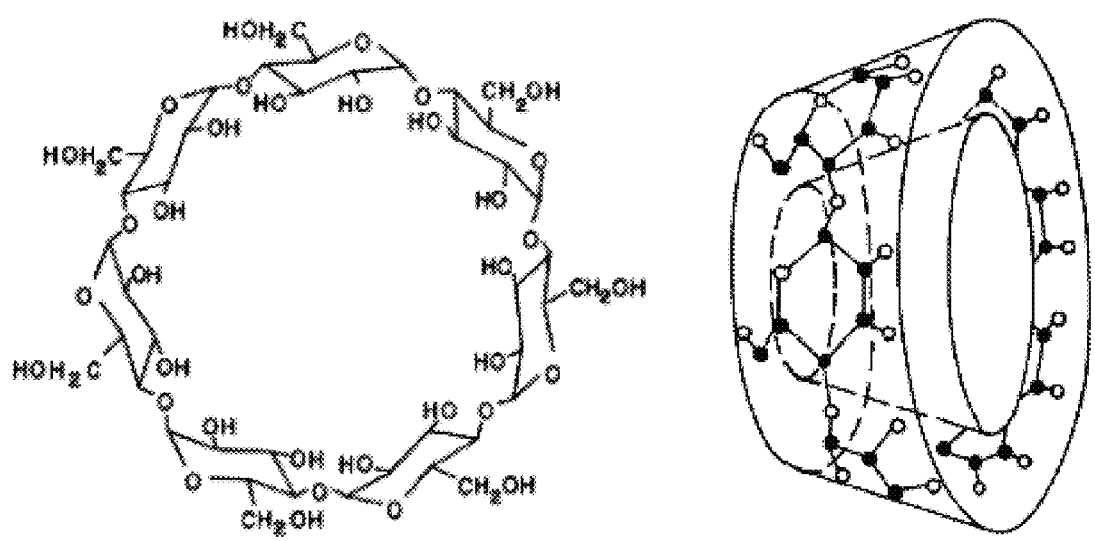
FIG. 1 shows the chemical structure and toroidal topology of beta-cyclodextrin molecule (see, for example Rasheed et al. (2008) Sci. Pharm. 76: 567-598).

It has been determined herein that cyclodextrins can encapsulate selective inhibitors of ATP production such as 3-halopyruvates (e.g., 3-BrPA), in order to stabilize the alkylating compound in an aqueous environment, as well as reduce the ability of nucleophilic entities in proteins to access it, thereby lowering its systemic toxicity and maintaining its alkylating ability. Such compositions are demonstrated herein in multiple in vitro cell lines, using different forms of cyclodextrins (e.g., beta and alpha) and at different ratios of active agent encapsulation relative to the cyclodextrin, and in in vivo animal tumor models. For example, such compositions are demonstrated herein to maintain the functional characteristics of the selective inhibitors of ATP production to kill cancer cells both in vitro and in vivo such that their activity can be preserved and protected for systemic administration until it reaches the target tissue, organ, and/or tumor while minimizing toxicity. This determination was unexpected because cyclodextrins are known to have a destabilizing effect on many compounds through direct catalysis, particularly with increasing pH (Rasheed et al. (2008) *Sci. Pharm.* 76: 567-598). Although this catalytic effect of cyclodextrins would have been expected to be great for 3-halopyruvates since they are halogenated derivatives of pyruvic acid, it was surprisingly determined that cyclodextrins actually protected and stabilized 3-BrPA. It was further surprisingly determined that cyclodextrins modified to replace one or more hydroxyl groups on one or more of its α-D-glucopyranoside units with ionizable groups resulting in negative charges (anions) stabilizes the 3-halopyruvates better than those having ionizable groups resulting in positive charges (cations) or unmodified cyclodextrins, such as unmodified alpha- or beta-cyclodextrin. Without being bound by theory, it is believed that anionic moieties on cyclodextrins force the halogen atom (e.g., bromine) of a halopyruvate (e.g., 3-BrPA) to sit in the cavity. It was also surprisingly determined that β-cyclodextrins encapsulate 3-BrPA in a form that protects and stabilizes 3-BrPA for in vivo efficacy especially and also in vitro efficacy significantly better than α-cyclodextrins.

Thus, the present invention provides compositions and kits comprising such 3-halopyruvate compounds encapsulated within cyclodextrins, as well as methods of making and using such compositions and kits.

A. Definitions

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The term "3-bromopyruvate" or "3-BrPA" refers to 3-bromopyruvate, analogs and derivatives of 3-brompyruvate, prodrugs of 3-bromopyruvate, metabolites of 3-bromopyruvate and salts thereof.

The term "administering" means providing a pharmaceutical agent or composition to a subject, and includes, but is not limited to, administering by a medical professional and self-administering.

The term "cancer" includes, but is not limited to, solid tumors and blood borne tumors. The term cancer includes diseases of the skin, tissues, organs, bone, cartilage, blood and vessels. The term "cancer" further encompasses primary and metastatic cancers.

The term "inhibit" or "inhibits" means to decrease, suppress, attenuate, diminish, arrest, or stabilize the development or progression of a disease, disorder, or condition, the activity of a biological pathway, or a biological activity, such as the growth of a solid malignancy, e.g., by at least 10%, 20%, 30%, 40%, 50%, 60%, 70%, 80%, 90%, 95%, 98%, 99%, or even 100% compared to an untreated control subject, cell, biological pathway, or biological activity or compared to the target, such as a growth of a solid malignancy, in a subject before the subject is treated. By the term "decrease" is meant to inhibit, suppress, attenuate, diminish, arrest, or stabilize a symptom of a cancer disease, disorder, or condition. It will be appreciated that, although not precluded, treating a disease, disorder or condition does not require that the disease, disorder, condition or symptoms associated therewith be completely eliminated.

The term "modulation" refers to upregulation (i.e., activation or stimulation), downregulation (i.e., inhibition or suppression) of a response, or the two in combination or apart.

The term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The term "pharmaceutically-acceptable salts" refers to the relatively non-toxic, inorganic and organic salts of compounds.

A "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, and the like).

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "subject suspected of having" means a subject exhibiting one or more clinical indicators of a disease or condition. In certain embodiments, the disease or condition is cancer. In certain embodiments, the cancer is leukemia or lymphoma.

The term "subject in need thereof" means a subject identified as in need of a therapy or treatment.

The terms "systemic administration," "administered systemically," "peripheral administration," and "administered peripherally" mean the administration of a compound, drug or other material other than directly into the central nervous system, such that it enters the patient's system and, thus, is subject to metabolism and other like processes, for example, subcutaneous administration.

The term "therapeutic agent" or "pharmaceutical agent" refers to an agent capable of having a desired biological effect on a host. Chemotherapeutic and genotoxic agents are examples of therapeutic agents that are generally known to be chemical in origin, as opposed to biological, or cause a therapeutic effect by a particular mechanism of action, respectively. Examples of therapeutic agents of biological origin include growth factors, hormones, and cytokines. A variety of therapeutic agents is known in the art and may be identified by their effects. Certain therapeutic agents are capable of regulating red cell proliferation and differentiation. Examples include chemotherapeutic nucleotides, drugs, hormones, non-specific (e.g. non-antibody) proteins, oligonucleotides (e.g., antisense oligonucleotides that bind to a target nucleic acid sequence (e.g., mRNA sequence)), peptides, and peptidomimetics.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The term "treating" a disease in a subject or "treating" a subject having a disease refers to subjecting the subject to a pharmaceutical treatment, e.g., the administration of a drug, such that at least one symptom of the disease is decreased or prevented from worsening.

The terms "tumor," "solid malignancy," or "neoplasm" refer to a lesion that is formed by an abnormal or unregulated growth of cells. Preferably, the tumor is malignant, such as that formed by a cancer.

B. Cyclodextrins

The term "cyclodextrin" refers to a family of cyclic oligosaccharides composed of 5 or more α-D-glucopyranoside units linked together by C1-C4 bonds having a toroidal topological structure, wherein the larger and the smaller openings of the toroid expose certain hydroxyl groups of the α-D-glucopyranoside units to the surrounding environment (e.g., solvent) (see, for examples, FIG. 1). The term "inert cyclodextrin" refers to a cyclodextrin containing α-D-glucopyranoside units having the basic formula $C_6H_{12}O_6$ and glucose structure without any additional chemical substitutions (e.g., α-cyclodextrin having 6 glucose monomers, β-cyclodextrin having 7 glucose monomers, and γ-cyclodextrin having 8 glucose monomers). The term "cyclodextrin internal phase" refers to the relatively less hydrophilic region enclosed within (i.e., encapsulated by) the toroid topology of the cyclodextrin structure. The term "cyclodextrin external phase" refers to the region not enclosed by the toroid topology of the cyclodextrin structure and can include, for example, the aqueous environment present during systemic administration in vivo or to the internal phase of a structure that itself encapsulates the selective ATP production inhibitor/cyclodextrin complex. Cyclodextrins are useful for solubilizing hydrophobic compositions (see, for example, Albers and Muller (1995) Crit. Rev. Therap. Drug Carrier Syst. 12:311-337; Zhang and Ma (2013) Adv. Drug Delivery Rev. 65:1215-1233; Laza-Knoerr et al. (2010) J. Drug Targ. 18:645-656; Challa et al. (2005) AAPS PharmSci. Tech. 6:E329-357; Uekama et al. (1998) Chem. Rev. 98:2045-2076; Szejtli (1998) Chem. Rev. 98:1743-1754; Stella and He (2008) Toxicol. Pathol. 36:30-42; Rajewski and Stella (1996) J. Pharm. Sci. 85:1142-1169; Thompson (1997) Crit. Rev. Therap. Drug Carrier Sys. 14:1-104; and Irie and Uekama (1997) J. Pharm. Sci. 86:147-162). Any substance located within the cyclodextrin internal phase is said to be "encapsulated."

As used herein, a cyclodextrin is useful according to the present invention so long as the cyclodextrins can encapsulate a selective ATP production inhibitor. In some embodiments, the cyclodextrin further bears ionizable (e.g., weakly basic and/or weakly acidic) functional groups to enhance the stabilization of the selective ATP production inhibitor. By protecting the stability of the selective ATP production inhibitor, it is meant that the selective ATP production inhibitor/cyclodextrin complex makes the selective ATP production inhibitor molecule more stable as seen by photo stability, shelf life stability, thermal stability, stability against intramolecular cyclization, stability to acid hydrolysis, stability against general degradation, and the like, as compared to the stability of a selective ATP production inhibitor molecule that is not in a complex with cyclodextrin.

For encapsulating a desired therapeutic agent, cyclodextrins can be selected and/or chemically modified according to the characteristics of the desired therapeutic agent and parameters for efficient, high-concentration loading therein. For example, it is preferable that the cyclodextrin itself have high solubility in water in order to facilitate loading of a therapeutic agent, such as a 3-halopyruvate. In some embodiments, the water solubility of the cyclodextrin is at least 10 mg/mL, 20 mg/mL, 30 mg/mL, 40 mg/mL, 50 mg/mL, 60 mg/mL, 70 mg/mL, 80 mg/mL, 90 mg/mL, 100 mg/mL or higher. Methods for achieving such enhanced water solubility are well known in the art.

In some embodiments, a large association constant with the therapeutic agent is preferable and can be obtained by selecting the number of glucose units in the cyclodextrin based on the size of the therapeutic agent (see, for example, Albers and Muller (1995) Crit. Rev. Therap. Drug Carrier Syst. 12:311-337; Stella and He (2008) Toxicol. Pathol. 36:30-42; and Rajewski and Stella (1996) J. Pharm. Sci. 85:1142-1169). As a result, the solubility (nominal solubility) of the therapeutic agent in the presence of cyclodextrin can be further improved. For example, the association constant of the cyclodextrin with the therapeutic agent can be 100, 200, 300, 400, 500, 600, 700, 800, 900, 1,000, or higher.

Derivatives formed by reaction with cyclodextrin hydroxyl groups (e.g., those lining the upper and lower ridges of the toroid of an inert cyclodextrin) are readily prepared and offer a means of modifying the physicochemical properties of the parent (inert) cyclodextrin. In some embodiments, the physicochemical properties of the inert cyclodextrin molecule or cyclodextrin molecule that is not complexed with a selective ATP production inhibitor differ from the properties of a cyclodextrin molecule complexed with the selective ATP production inhibitor. Accordingly, the selective ATP production inhibitor molecules complexed with cyclodextrin can be characterized by observing changes in solubility, chemical reactivity, UV/VIS absorbance, drug retention, chemical stability, and the like. For example, it has been determined herein that modifying hydroxyl groups, such as those facing away from the cyclodextrin interior phase, can be replaced with ionizable chemical groups to facilitate loading of therapeutic agents, such as poorly soluble or hydrophobic agents, within the modified cyclodextrins and stabilization thereof. In one embodiment, a modified cyclodextrin having at least one hydroxyl group substituted with an ionizable chemical group will result in a charged moiety under certain solvent (e.g., pH) conditions. The term "charged cyclodextrin" refers to a cyclodextrin having one or more of its hydroxyl groups substituted with a charged moiety and the moiety bearing a charge. Such a moiety can itself be a charged group or it can comprise an organic moiety (e.g., a $C_i$-$C_6$ alkyl or $C_i$-$C_6$ alkyl ether moiety) substituted with one or more charged moieties.

In one embodiment, the "ionizable" or "charged" moieties are weakly ionizable. Weakly ionizable moieties are those that are either weakly basic or weakly acidic. Weakly basic functional groups (X) have a $pK_a$ of between about 6.0-9.0, 6.5-8.5, 7.0-8.0, 7.5-8.0, and any range in between inclusive according to $CH_3$—X. Similarly, weakly acidic functional groups (Y) have a log dissociation constant ($pK_a$) of between about 3.0-7.0, 4.0-6.5, 4.5-6.5, 5.0-6.0, 5.0-5.5, and any range in between inclusive according to $CH_3$—Y. The pKa parameter is a well-known measurement of acid/base properties of a substance and methods for pKa determination are conventional and routine in the art. For example, the pKa values for many weak acids are tabulated in reference books of chemistry and pharmacology. See, for example, IUPAC Handbook of Pharmaceutical Salts, ed. by P. H. Stahl and C. G Wermuth, Wiley-VCH, 2002; CRC Handbook of Chemistry and Physics, 82nd Edition, ed. by D. R. Lide, CRC Press, Florida, 2001, p. 8-44 to 8-56. Since cyclodextrins with more than one ionizable group have pKa of the second and subsequent groups each denoted with a subscript.

Representative anionic moieties include, without any limitation, succinyl, carboxylate, carboxymethyl, sulfonyl, phosphate, sulfoalkyl ether, sulphate carbonate, thiocarbonate, thiocarbonate, phosphate, phosphonate, sulfonate, nitrate, and borate groups.

Representative cationic moieties include, without limitation, amino, guanidine, and quaternary ammonium groups.

In another embodiment, the modified cyclodextrin is a "polyanion" or "polycation." A polyanion is a modified cyclodextrin having more than one negatively charged group resulting in net negative ionic charger of more than two units. A polycation is a modified cyclodextrin having more than one positively charged group resulting in net positive ionic charger of more than two units.

In another embodiment, the modified cyclodextrin is a "chargeable amphiphile." By "chargeable" is meant that the amphiphile has a pK in the range pH 4 to pH 8 or 8.5. A chargeable amphiphile may therefore be a weak acid or base. By "amphoteric" herein is meant a modified cyclodextrin having a ionizable groups of both anionic and cationic character wherein: 1) at least one, and optionally both, of the cation and anionic amphiphiles is chargeable, having at least one charged group with a pK between 4 and 8 to 8.5, 2) the cationic charge prevails at pH 4, and 3) the anionic charge prevails at pH 8 to 8.5.

In some embodiments, the "ionizable" or "charged" cyclodextrins as a whole, whether polyionic, amphiphilic, or otherwise, are weakly ionizable (i.e., have a $pKa_1$ of between about 4.0-8.5, 4.5-8.0, 5.0-7.5, 5.5-7.0, 6.0-6.5, and any range in between inclusive).

Any one, some, or all hydroxyl groups of any one, some or all α-D-glucopyranoside units of a cyclodextrin can be modified to an ionizable chemical group as described herein. Since each cyclodextrin hydroxyl group differs in chemical reactivity, reaction with a modifying moiety can produce an amorphous mixture of positional and optical isomers. Alternatively, certain chemistry can allow for pre-modified α-D-glucopyranoside units to be reacted to form uniform products.

The aggregate substitution that occurs is described by a term called the degree of substitution. For example, a 6-ethylenediamino-β-cyclodextrin with a degree of substitution of seven would be composed of a distribution of isomers of 6-ethylenediamino-β-cyclodextrin in which the average number of ethylenediamino groups per 6-ethylenediamino-β-cyclodextrin molecule is seven. Degree of substitution can be determined by mass spectrometry or nuclear magnetic resonance spectroscopy. Theoretically, the maximum degree of substitution is 18 for α-cyclodextrin, 21 for β, and 24 for γ-cyclodextrin, however, substituents themselves having hydroxyl groups present the possibility for additional hydroxylalkylations. The degree of substitution can be 1, 2, 3, 4, 5, 6, 7, 8, 9, 10, 11, 12, 13, 14, 15, 16, 17, 18, 19, 20, 21, 22, 23, 24, or more and can encompass complete substitution.

Another parameter is the stereochemical location of a given hydroxyl substitution. In one embodiment, at least one hydroxyl facing away from the cyclodextrin interior is substituted with an ionizable chemical group. For example, the C2, C3, C6, C2 and C3, C2 and C6, C3 and C6, and all three of C2-C3-C6 hydroxyls of at least one α-D-glucopyranoside unit are substituted with an ionizable chemical group. Such carbon positions are well known in the art. For example, the CH2OH moiety shown in FIG. 1 of each α-D-glucopyranoside unit represents the C6 carbon. Any such combination of hydroxyls can similarly be combined with at least two, three, four, five, six, seven, eight, nine, ten, eleven, up to all of the α-D-glucopyranoside units in the modified cyclodextrin as well as in combination with any degree of substitution described herein.

It is also acceptable to combine one or more of the cyclodextrins described herein.

C. Selective Inhibitors of ATP Production and Related Compounds

Some embodiments of the present invention relate to the encapsulation of selective inhibitors of ATP production within cyclodextrins. The term "selective inhibitors of ATP production" refers to anti-metabolite agents that inhibit ATP production by interfering with the enzymatic process of generating ATP (e.g., GAPDH inhibitors such as 3-halopyruvates like 3-bromopyruvate). In some embodiments, the selective inhibitor of ATP production is an "antineoplastic alkylating agent," which refers to an agent used in cancer treatment that causes replacement of hydrogen by an alkyl group. As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom. Representative alkyl groups include, but are not limited to, methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, and the like, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl. Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

In one embodiment, selective inhibitors of ATP production are generally represented by the formula:

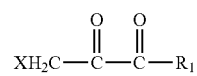

wherein X represents a halide, a sulfonate, a carboxylate, an alkoxide, or an amine oxide. In certain embodiments, X is a halide selected from the group consisting of: fluoride, bromide, chloride, and iodide. In one embodiment, the inhibitor is a 3-halopyruvate. In certain other embodiments, the 3-halopyruvate is selected from the group consisting of: 3-fluoropyruvate, 3-chloropyruvate, 3-bromopyruvate and 3-iodopyruvate. In one embodiment, the 3-halopyruvate is 3-bromopyruvate. In other embodiments, X is a sulfonate and may be selected from the group consisting of: triflate, mesylate and tosylate. In yet another embodiment, X is an amine oxide is dimethylamine oxide. In certain embodiments $R_1$ represents OR, H, $N(R'')_2$, C1-C6 alkyl, C6-C12 aryl, C1-C6 heteroalkyl, or a C6-C12 heteroaryl. Independently, in other embodiments, R" represents H, C1-C6 alkyl, or C6-C12 aryl. Independently, in still other embodiments, R represents H, alkali metal, C1-C6 alkyl, C6-C12 aryl or C(O)R'; and R' represents H, C1-C20 alkyl or C6-C12 aryl.

In a preferred embodiment, the invention further provides inhibitors of ATP production represented by general formula:

wherein X represents a halide, a sulfonate, a carboxylate, an alkoxide, or an amine oxide. In certain embodiments, X is a halide and may be selected from the group consisting of: fluoride, bromide, chloride, and iodide. In one embodiment, the inhibitor is 3-halopyruvate. In certain embodiments, the 3-halopyruvate is selected from the group consisting of: 3-fluoropyruvate, 3-chloropyruvate, 3-bromopyruvate and 3-iodopyruvate. In one embodiment, the 3-halopyruvate is 3-bromopyruvate. In other embodiments, X is a sulfonate selected from the group consisting of: triflate, mesylate and tosylate. In yet another embodiment, X is an amine oxide is dimethylamine oxide.

Other analogs, derivatives, prodrugs, metabolites and salts thereof of 3-bromopyruvate can also be used, provided that these compounds or compositions have an anticancer effect that is statistically similar to that of 3-bromopyruvate. When referring herein to a treatment using 3-bromopyruvate, it should be understood that the treatment may also be conducted with analogs, derivatives, prodrugs, metabolites and salts of 3-bromopyruvate, where applicable.

D. Cyclodextrin/ATP Inhibitor Compositions

The present invention provides pharmaceutical compositions comprising selective inhibitors of ATP production described above encapsulated within inert and/or modified cyclodextrins. Such complexes are referred to herein as cyclodextrin/ATP inhibitor compositions. The ratio of selective inhibitor of ATP production to cyclodextrin may be 1:1 such that one inhibitor molecule forms a complex with one cyclodextrin molecule. Alternatively, the ratio can be 2:1, 3:1, 4:1, 5:1, or more.

In one aspect, the present invention provides pharmaceutically acceptable compositions which comprise a therapeutically-effective amount of one or more such cyclodextrin/ATP inhibitors described above, formulated together with one or more pharmaceutically acceptable carriers (additives) and/or diluents. In another aspect the compositions can be administered as such or in admixtures with pharmaceutically acceptable carriers and can also be administered in conjunction with other anti-cancer therapies, such as chemotherapeutic agents, scavenger compounds, radiation therapy, biologic therapy, and the like. Conjunctive therapy thus includes sequential, simultaneous and separate, or co-administration of the composition, wherein the therapeutic effects of the first administered has not entirely disappeared when the subsequent compound is administered.

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

As set out above, certain embodiments of the selective ATP inhibitors or cyclodextrin/ATP inhibitor compositions may contain a basic functional group, such as amino or alkylamino, and are, thus, capable of forming pharmaceutically-acceptable salts with pharmaceutically-acceptable acids. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the selective ATP inhibitors or cyclodextrin/ATP inhibitor compositions of the present invention may contain one or more acidic functional groups and, thus, are capable of forming pharmaceutically-acceptable salts with pharmaceutically-acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Cyclodextrin/ATP inhibitor composition formulations include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect.

In certain embodiments, a formulation of cyclodextrin/ATP inhibitor compositions can comprise other carriers to allow more stability, to allow more stability, different releasing properties in vivo, targeting to a specific site, or any other desired characteristic that will allow more effective delivery of the complex to a subject or a target in a subject, such as, without limitation, liposomes, microspheres, nanospheres, nanoparticles, bubbles, micelle forming agents, e.g., bile acids, and polymeric carriers, e.g., polyesters and polyanhydrides. In certain embodiments, an aforementioned formulation renders orally bioavailable a compound of the present invention.

Liquid dosage formulations of cyclodextrin/ATP inhibitor compositions include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an active ingredient. A cyclodextrin/ATP inhibitor composition of the present invention may also be administered as a bolus, electuary or paste.

In solid dosage forms (e.g., capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. Compositions may also be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Formulations for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations which are suitable for vaginal administration also include pessaries, tampons, creams, gels, pastes, foams or spray formulations containing such carriers as are known in the art to be appropriate.

Dosage forms for the topical or transdermal administration of a cyclodextrin/ATP inhibitor composition of the present invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions suitable for parenteral administration can comprise sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In certain embodiments, the above-described pharmaceutical compositions can be combined with other pharmacologically active compounds ("second active agents") known in the art according to the methods and compositions provided herein. Second active agents can be large molecules (e.g., proteins) or small molecules (e.g., synthetic inorganic, organometallic, or organic molecules). In one embodiment, second active agents independently or synergistically help to treat cancer.

For example, chemotherapeutic agents are anti-cancer agents. The term chemotherapeutic agent includes, without limitation, platinum-based agents, such as carboplatin and cisplatin; nitrogen mustard alkylating agents; nitrosourea alkylating agents, such as carmustine (BCNU) and other alkylating agents; antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as taxanes (e.g., docetaxel and paclitaxel), aldesleukin, interleukin-2, etoposide (VP-16), interferon alfa, and tretinoin (ATRA); antibiotic natural antineoplastics, such as bleomycin, dactinomycin, daunorubicin, doxorubicin, and mitomycin; and vinca alkaloid natural antineoplastics, such as vinblastine and vincristine.

Further, the following drugs may also be used in combination with an antineoplastic agent, even if not considered antineoplastic agents themselves: dactinomycin; daunorubicin HCl; docetaxel; doxorubicin HCl; epoetin alfa; etoposide (VP-16); ganciclovir sodium; gentamicin sulfate; interferon alfa; leuprolide acetate; meperidine HCl; methadone HCl; ranitidine HCl; vinblastin sulfate; and zidovudine (AZT). For example, fluorouracil has recently been formulated in conjunction with epinephrine and bovine collagen to form a particularly effective combination.

Still further, the following listing of amino acids, peptides, polypeptides, proteins, polysaccharides, and other large molecules may also be used: interleukins 1 through 18, including mutants and analogues; interferons or cytokines, such as interferons α, β, and γ; hormones, such as luteinizing hormone releasing hormone (LHRH) and analogues and, gonadotropin releasing hormone (GnRH); growth factors, such as transforming growth factor-β (TGF-β), fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-α & β (TNF-α & β); invasion inhibiting factor-2 (IIF-2); bone morphogenetic proteins 1-7 (BMP 1-7); somatostatin; thymosin-α-1; γ-globulin; superoxide dismutase (SOD); complement factors; anti-angiogenesis factors; antigenic materials; and prodrugs.

Chemotherapeutic agents for use with the compositions and methods of treatment described herein include, but are not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechloretamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylomithine (DMFO); retinoids such as retinoic acid; capecitabine; and pharmaceutically acceptable salts, acids or derivatives of any of the above.

In another embodiment, the composition of the invention may comprise other biologically active substances, including therapeutic drugs or pro-drugs, for example, other chemotherapeutic agents, scavenger compounds, antibiotics, anti-virals, anti-fungals, anti-inflammatories, vasoconstrictors and anticoagulants, antigens useful for cancer vaccine applications or corresponding pro-drugs.

Exemplary scavenger compounds include, but are not limited to thiol-containing compounds such as glutathione, thiourea, and cysteine; alcohols such as mannitol, substituted phenols; quinones, substituted phenols, aryl amines and nitro compounds.

Various forms of the chemotherapeutic agents and/or other biologically active agents may be used. These include, without limitation, such forms as uncharged molecules, molecular complexes, salts, ethers, esters, amides, and the like, which are biologically active.

E. Methods of Making Cyclodextrin/ATP Inhibitor Compositions

Methods of preparing cyclodextrin/ATP inhibitor compositions and formulations thereof include the step of bringing into association a compound of the present invention with the carrier and, optionally, one or more accessory ingredients. In general, the formulations are prepared by uniformly and intimately bringing into association a selective inhibitor of ATP production described herein with a cyclodextrin. Generally, such complexes can be obtained by agitating and mixing the cyclodextrin (e.g., a solution containing the cyclodextrin) upon dropwise addition of the therapeutic agent (e.g., a solution containing the selective inhibitor of ATP production) or vice versa. Many mixing means are known in the art to aid in combining the inhibitor and cyclodextrin for example, without limitation, sonication, vortexing, stirring, heating, co-precipitation, neutralization, slurrying, kneading, grinding, and the like. It is possible to use a substance dissolved in a solvent or a solid substance as the therapeutic agent according to the physical properties of the therapeutic agent. There are no particular limitations on the solvent, and one can use, for example, a substance identical to the cyclodextrin external phase. The amount of the therapeutic agent that is mixed with the cyclodextrin can be equimolar quantities or in different ratios depending on the desired level of incorporation. In some embodiments, absolute amounts of the selective inhibitor of ATP production can range between 0.001 to 10 mol equivalents, 0.01 to 1 mol equivalent, or any range inclusive relative to the amount of cyclodextrin. Also, there are no particular limitations on the heating temperature. For example, 5° C. or higher, room temperature or higher (e.g., 20° C. or higher is also preferable), are all acceptable.

Well-known methods exist for removing any undesired or unincorporated complexes or compositions, such as therapeutic agent not encapsulated by cyclodextrins or therapeutic agent cyclodextrin complexes not encapsulated by liposomes. Representative examples include, without limitation, dialysis, centrifugal separation, and gel filtration. Dialysis can be conducted, for example, using a dialysis membrane. As a dialysis membrane, one may cite a membrane with molecular weight cut-off such as a cellulose tube or Spectra/Por. With respect to centrifugal separation, centrifugal acceleration any be conducted preferably at 100,000 g or higher, and more preferably at 300,000 g or higher. Gel filtration may be carried out, for example, by conducting fractionation based on molecular weight using a column such as Sephadex or Sepharose.

In some cases, in order to prolong the effect of a drug, it is desirable to modify (e.g., slow) the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form can be accomplished by dissolving or suspending the drug in an oil vehicle. In some embodiments, the cyclodextrin-encapsulated selective ATP inhibitor compositions described herein can be loaded into liposomes.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

F. Therapeutic Methods

The present invention further provides novel therapeutic methods of preventing, delaying, reducing, and/or treating a cancer, including a cancerous tumor. In one embodiment, a method of treatment comprises administering to a subject (e.g., a subject in need thereof), an effective amount of a cyclodextrin/selective ATP production inhibitor composition. A subject in need thereof may include, for example, a subject who has been diagnosed with a tumor, including a pre-cancerous tumor, a cancer, or a subject who has been treated, including subjects that have been refractory to the previous treatment.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition, or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

The methods of the present invention may be used to treat any cancerous or pre-cancerous tumor. In certain embodiments, the cancerous tumor has a highly glycolytic phenotype. For example, highly glycolytic tumors may be located in a tissue selected from brain, colon, urogenital, lung, renal, prostate, pancreas, liver, esophagus, stomach, hematopoietic, breast, thymus, testis, ovarian, skin, bone marrow and/or uterine tissue. In some embodiments, methods and compositions of the present invention may be used to treat any cancer. Cancers that may treated by methods and compositions of the invention include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The compositions described herein may be delivered by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

The terms "systemic administration," "administered systemically," "peripheral administration," and "administered peripherally" as used herein mean the administration of the selective ATP production inhibitor/cyclodextrin complex such that it enters the patient's system and, thus, is subject to metabolism and other like processes.

The terms "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

In certain embodiments the pharmaceutical compositions are delivered generally (e.g., via oral or parenteral administration). In certain other embodiments the pharmaceutical compositions are delivered locally through direct injection into a tumor or direct injection into the tumor's blood supply (e.g., arterial or venous blood supply). In some embodiments, the pharmaceutical compositions are delivered by both a general and a local administration. For example, a subject with a tumor may be treated through direct injection of a composition containing a composition described herein into the tumor or the tumor's blood supply in combination with oral administration of a pharmaceutical composition of the present invention. If both local and general administration is used, local administration can occur before, concurrently with and/or after general administration.

In certain embodiments, the methods of treatment of the present invention, including treating a cancerous or pre-cancerous tumor comprise administering compositions described herein in combination with a second agent and/or therapy to the subject. By "in combination with" is meant the administration of the selective ATP production inhibitor/cyclodextrin complexes with one or more therapeutic agents either simultaneously, sequentially, or a combination thereof. Therefore, a subject administered a combination of the selective ATP production inhibitor/cyclodextrin complexes and/or therapeutic agents, can receive the selective ATP production inhibitor/cyclodextrin complexes as described herein, and one or more therapeutic agents at the same time (i.e., simultaneously) or at different times (i.e., sequentially, in either order, on the same day or on different days), so long as the effect of the combination of both agents is achieved in the subject. When administered sequentially, the agents can be administered within 1, 5, 10, 30, 60, 120, 180, 240 mins. or longer of one another. In other embodiments, agents administered sequentially, can be administered within 1, 5, 10, 15, 20 or more days of one another.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered agent is not diminished by the sequential, simultaneous or separate administration of the subsequent agent(s).

Such methods in certain embodiments comprise administering pharmaceutical compositions comprising compositions described herein in conjunction with one or more chemotherapeutic agents and/or scavenger compounds, including chemotherapeutic agents described herein, as well as other agents known in the art. Conjunctive therapy includes sequential, simultaneous and separate, or co-administration of the composition in a way that the therapeutic effects of the first selective ATP inhibitor administered have not entirely disappeared when the subsequent compound is administered. In one embodiment, the second agent is a chemotherapeutic agent. In another embodiment, the second agent is a scavenger compound. In another embodiment, the second agent is radiation therapy. In a further embodiment, radiation therapy may be administered in addition to the composition. In certain embodiments, the second agent may be co-formulated in the separate pharmaceutical composition.

In some embodiments, the subject pharmaceutical compositions of the present invention will incorporate the substance or substances to be delivered in an amount sufficient to deliver to a patient a therapeutically effective amount of an incorporated therapeutic agent or other material as part of a prophylactic or therapeutic treatment. The desired concentration of the active compound in the particle will depend on absorption, inactivation, and excretion rates of the drug as well as the delivery rate of the compound. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Dosage may be based on the amount of the composition or active compound thereof (e.g., selective inhibitor of ATP production) per kg body weight of the patient. For example, a range of amounts of compositions or compound encapsulated therein are contemplated, including about 0.001, 0.01, 0.1, 0.5, 1, 10, 15, 20, 25, 50, 75, 100, 150, 200 or 250 mg or more of such compositions per kg body weight of the patient. Other amounts will be known to those of skill in the art and readily determined.

In certain embodiments, the dosage of the composition or active compound thereof (e.g., selective inhibitor of ATP production) will generally be in the range of about 0.001 mg to about 250 mg per kg body weight, specifically in the range of about 50 mg to about 200 mg per kg, and more specifically in the range of about 100 mg to about 200 mg per kg. In one embodiment, the dosage is in the range of about 150 mg to about 250 mg per kg. In another embodiment, the dosage is about 200 mg per kg.

In some embodiments the molar concentration of the composition or active compound thereof (e.g., selective inhibitor of ATP production) in a pharmaceutical composition will be less than or equal to about 2.5 M, 2.4 M, 2.3 M, 2.2 M, 2.1 M, 2 M, 1.9 M, 1.8 M, 1.7 M, 1.6 M, 1.5 M, 1.4 M, 1.3 M, 1.2 M, 1.1 M, 1 M, 0.9 M, 0.8 M, 0.7 M, 0.6 M, 0.5 M, 0.4 M, 0.3 M or 0.2 M. In some embodiments the concentration of the composition or active compound thereof (e.g., selective inhibitor of ATP production) will be less than or equal to about 0.10 mg/ml, 0.09 mg/ml, 0.08 mg/ml, 0.07 mg/ml, 0.06 mg/ml, 0.05 mg/ml, 0.04 mg/ml, 0.03 mg/ml or 0.02 mg/ml.

Alternatively, the dosage may be determined by reference to the plasma concentrations of the composition or active compound thereof (e.g., selective inhibitor of ATP production). For example, the maximum plasma concentration ($C_{max}$) and the area under the plasma concentration-time curve from time 0 to infinity (AUC (0-4)) may be used. Dosages for the present invention include those that produce the above values for $C_{max}$ and AUC (0-4) and other dosages resulting in larger or smaller values for those parameters.

Actual dosage levels of the active ingredients in the compositions of the present invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular therapeutic agent in the formulation employed, or the ester, salt or amide thereof, the route of administration, the time of administration, the rate of excretion or metabolism of the particular therapeutic agent being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above.

If desired, the effective daily dose of the active compound may be administered as two, three, four, five, six or more sub-doses administered separately at appropriate intervals throughout the day, optionally, in unit dosage forms.

The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. All aspects of the treatment, including supplements, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments, for example, to the amount(s) of agent administered and to the time of administration may be made based on these reevaluations.

Treatment may be initiated with smaller dosages which are less than the optimum dose of the compound. Thereafter, the dosage may be increased by small increments until the optimum therapeutic effect is attained.

As described above, the composition or active compound thereof (e.g., selective inhibitor of ATP production) may be administered in combination with radiation therapy. An optimized dose of radiation therapy may be given to a subject as a daily dose. Optimized daily doses of radiation therapy may be, for example, from about 0.25 to 0.5 Gy, about 0.5 to 1.0 Gy, about 1.0 to 1.5 Gy, about 1.5 to 2.0 Gy, about 2.0 to 2.5 Gy, and about 2.5 to 3.0 Gy. An exemplary daily dose may be, for example, from about 2.0 to 3.0 Gy. A higher dose of radiation may be administered, for example, if a tumor is resistant to lower doses of radiation. High doses of radiation may reach, for example, 4 Gy. Further, the total dose of radiation administered over the course of treatment may, for example, range from about 50 to 200 Gy. In an exemplary embodiment, the total dose of radiation administered over the course of treatment ranges, for example, from about 50 to 80 Gy. In certain embodiments, a dose of radiation may be given over a time interval of, for example, 1, 2, 3, 4, or 5 mins, wherein the amount of time is dependent on the dose rate of the radiation source.

In certain embodiments, a daily dose of optimized radiation may be administered, for example, 4 or 5 days a week, for approximately 4 to 8 weeks. In an alternate embodiment, a daily dose of optimized radiation may be administered daily seven days a week, for approximately 4 to 8 weeks. In certain embodiments, a daily dose of radiation may be given a single dose. Alternately, a daily dose of radiation may be given as a plurality of doses. In a further embodiment, the optimized dose of radiation may be a higher dose of radiation than can be tolerated by the patient on a daily base. As such, high doses of radiation may be administered to a patient, but in a less frequent dosing regimen.

The types of radiation that may be used in cancer treatment are well known in the art and include electron beams, high-energy photons from a linear accelerator or from radioactive sources such as cobalt or cesium, protons, and neutrons. An exemplary ionizing radiation is an x-ray radiation.

Methods of administering radiation are well known in the art. Exemplary methods include, but are not limited to, external beam radiation, internal beam radiation, and radiopharmaceuticals. In external beam radiation, a linear accelerator is used to deliver high-energy x-rays to the area of the body affected by cancer. Since the source of radiation originates outside of the body, external beam radiation can be used to treat large areas of the body with a uniform dose of radiation. Internal radiation therapy, also known as brachytherapy, involves delivery of a high dose of radiation to a specific site in the body. The two main types of internal radiation therapy include interstitial radiation, wherein a source of radiation is placed in the effected tissue, and intracavity radiation, wherein the source of radiation is placed in an internal body cavity a short distance from the affected area. Radioactive material may also be delivered to tumor cells by attachment to tumor-specific antibodies. The radioactive material used in internal radiation therapy is typically contained in a small capsule, pellet, wire, tube, or implant. In contrast, radiopharmaceuticals are unsealed sources of radiation that may be given orally, intravenously or directly into a body cavity.

Radiation therapy may also include stereotactic surgery or stereotactic radiation therapy, wherein a precise amount of radiation can be delivered to a small tumor area using a linear accelerator or gamma knife and three dimensional conformal radiation therapy (3DCRT), which is a computer assisted therapy to map the location of the tumor prior to radiation treatment.

Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the cyclodextrin-encapsulated selective ATP inhibitor compositions described herein relative to the selective ATP inhibitor without any cyclodextrin encapsulation. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the cyclodextrin-encapsulated selective ATP inhibitor compositions described herein relative to the selective ATP inhibitor without any cyclodextrin encapsulation. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the cyclodextrin-encapsulated selective ATP inhibitor compositions described herein relative to the selective ATP inhibitor without any cyclodextrin encapsulation. Although compounds that exhibit toxic side effects may be used, care should be taken to design a delivery system that targets the compounds to the desired site in order to reduce side effects.

In some embodiments, the presently disclosed methods produce at least about a 10%, 15%, 20%, 25%, 30%, 35%, 40%, 45%, 50%, 55%, 60%, 65%, 70%, 75%, 80%, 85%, 90%, 95%, or even 100% inhibition of cancer cell growth in an assay.

In any of the above-described methods, the administering of the selective ATP production inhibitor/cyclodextrin complexes can result in at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy in a subject, compared to the solid malignancy before administration of the selective ATP production inhibitor/cyclodextrin complexes.

In some embodiments, the therapeutically effective amount of a complex of a selective ATP production inhibitor/cyclodextrin is administered prophylactically to prevent a solid malignancy from forming in the subject.

In some embodiments, the subject is human. In other embodiments, the subject is non-human, such as a mammal.

The data obtained from the cell culture assays and animal studies may be used in formulating a range of dosage for use in humans. The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For agents of the present invention, the therapeutically effective dose may be estimated initially from cell culture assays. A dose may be formulated in animal models to achieve a circulating plasma concentration range that includes the $IC_{50}$ as determined in cell culture. Such information may be used to more accurately determine useful doses in humans. Levels in plasma may be measured, for example, by high performance liquid chromatography.

G. kit

The selective ATP production inhibitor/cyclodextrin complexes and compositions described herein can be assembled into kits or pharmaceutical systems for use in treating or preventing a disease, such as cancer. In some embodiments, the 3-BrPA-cyclodextrin complex and compositions can be used to prevent or treat solid malignancies caused by a cancer. In general, a presently disclosed kit contains some or all of the components, reagents, supplies, and the like to practice a method according to the presently disclosed subject matter. The kit typically comprises an effective amount of complex to prevent, delay, reduce, or treat an unwanted disease (e.g., a solid malignancy). In one embodiment, a kit comprises at least one container (e.g., a carton, bottle, vial, tube, or ampoule) comprising a selective ATP production inhibitor/cyclodextrin complex and/or compositions thereof described herein. Typically, the complex and/or compositions will be supplied in one or more container, each container containing an effective amount of complex to allow a solid malignancy to regress, slow, or be arrested.

Accordingly, in some embodiments, the presently disclosed subject matter provides a kit comprising at least one selective ATP production inhibitor encapsulated within at least one cyclodextrin carrier. In other embodiments, the kit further comprises a set of instructions for using the at least one selective ATP production inhibitor encapsulated within the at least one cyclodextrin carrier.

It may be desirable to store the selective ATP production inhibitor and cyclodextrin separately and then combine them before use. Accordingly, in still other embodiments, the kit comprises at least one selective ATP production inhibitor in one container and at least one cyclodextrin carrier in another container.

EXEMPLIFICATION

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1: Materials and Methods for Examples 2-3

A. General Method for Synthesis of Modified β-Cyclodextrins

Succinyl-β-cyclodextrins were purchased from Sigma Chemical (St. Louis, Mo., USA; Catalog No. 85990). Unmodified β-cyclodextrin and α-cyclodextrin were purchased (Sigma-Aldrich, St. Louis, Mo.).

However, succinylated cyclodextrins can also be synthesized. For example, β-cyclodextrin (Sigma-Aldrich, St. Louis, Mo.) was mono-tosylated with 0.9 molar equivalent of tosyl chloride in pyridine at the primary 6' hydroxyl group to afford the corresponding tosylate, which was converted to the iodo-derivative by treatment with sodium iodide in acetone. The iodo derivative was converted to the desired 6' aminated cyclodextrin by heating at 80° C. for 8-12 hours with the appropriate amine (Tang and Ng (2008) *Nat. Protocol.* 3:691-697). 6' mono-succinyl-β-cyclodextrin was synthesized by treatment of parent β-cyclodextrin with 0.9 equivalents of succinic anhydride in DMF (Cucinotta et al. (2005) *J. Pharmaceut. Biomed. Anal.* 37:1009-1014). The product was precipitated in acetone and purified by HPLC before use.

The pH range with optimal stability is pH 4-9.

B. General Procedure of Preparation of Encapsulated Complexes

A 1:1 ratio of 3-BrPA encapsulated within succinyl-β-cyclodextrins was prepared. 3-BrPA (150 mg, 1 mmol) was added in small portions (10 mg each) to a stirring solution of succinyl-beta-cyclodextrin (1,500 mg in distilled water). After complete addition, the solution was sonicated for 1 hour at room temperature. The sonicated solution was then allowed to shake overnight on a thermomixer at 25° C., flash frozen in a dry ice-acetone bath, and lyophilized.

Similarly, a 2:1 ratio of 3-BrPA encapsulated within succinyl-β-cyclodextrins was prepared. 3-BrPA (166 mg, 1 mmol) was added in small portions (10 mg each) to a stirring solution of succinyl-beta-cyclodextrin (918 mg in 20 ml distilled water). After complete addition, the solution was sonicated for 1 hour at room temperature. The sonicated solution was then allowed to shake overnight on a thermomixer at 25° C., flash frozen in a dry ice-acetone bath, and lyophilized.

In addition, a 1:1 ratio of 3-BrPA encapsulated within α-cyclodextrins (see structure below) was prepared. 3-BrPA (166 mg, 1 mmol) was added in small portions (10 mg each) to a stirring solution of alpha-cyclodextrin (972 mg, 1 mmol in 10 ml distilled water). After complete addition, the solution was sonicated for 1 hour at room temperature. The sonicated solution was then allowed to shake overnight on a thermomixer at 25° C., flash frozen in a dry ice-acetone bath, and lyophilized. Non-GRAS and GRAS versions were used with similar results.

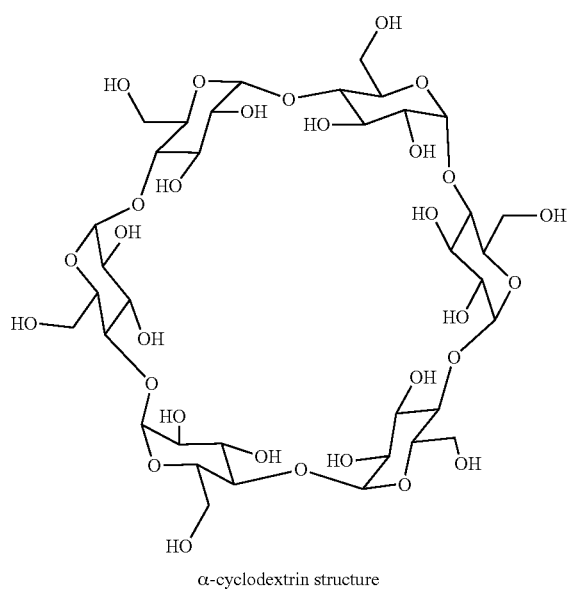 [SMILES: OCC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O]

α-cyclodextrin structure

It was surprisingly determined that cyclodextrins modified to replace one or more hydroxyl groups on one or more of its α-D-glucopyranoside units with ionizable groups resulting in negative charges (anions) stabilizes the 3-halopyruvates better than those having ionizable groups resulting in positive charges (cations) or unmodified cyclodextrins, such as unmodified alpha- or beta-cyclodextrin. It was also surprisingly determined that β-cyclodextrins encapsulate 3-BrPA in a form that protects and stabilizes 3-BrPA for in vivo efficacy especially and also in vitro efficacy significantly better than α-cyclodextrins.

In addition, in vitro cell culture and in vivo mouse treatments for were prepared and performed as described above and below for succinyl-β-cyclodextrins encapsulating 3-BrPA. using generally recognized as safe (GRAS) versions of β-cyclodextrins (e.g., hydroxypropyl-β-cyclodextrin having a level of substitution of 3-5 such as that shown in chemical form below) encapsulating 3-BrPA and the results were similar to those described for succinyl-β-cyclodextrins encapsulating 3-BrPA.

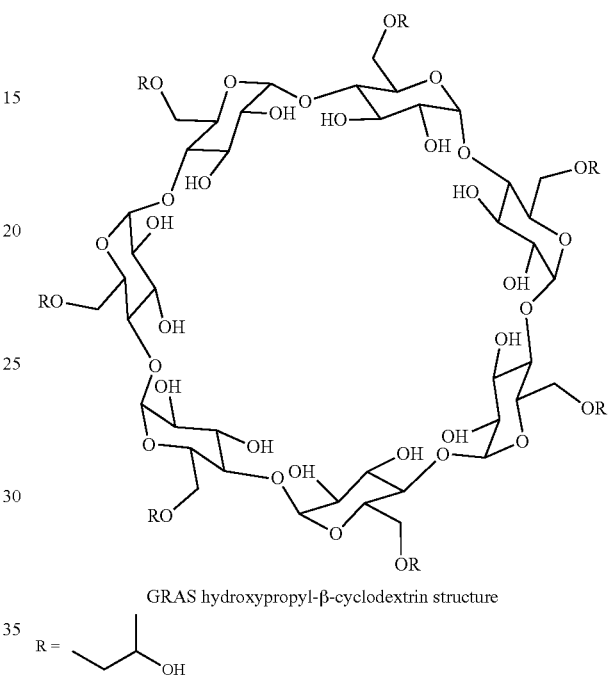

GRAS hydroxypropyl-β-cyclodextrin structure

C. In Vitro Cell Culture

3-BrPA and β-cyclodextrin (vehicle) were purchased from Sigma Chemical (St. Louis, Mo., USA). For the viability assay, MiaPaCa-2 and Suit-2 cells were seeded in triplicates in 96-well plates at a density of $5 \times 10^3$ cells per well. After 12 hours, cells were treated with increasing concentrations of 3-BrPA, CD-3BrPA (0-150 μm) and the vehicle. Intracellular ATP levels were measured using a Cell Titer-Glo Luminescence Cell Viability assay kit (Promega, Durham, N.C., USA) according to the manufacturer's protocol. The measurements were performed at 24 hours and 72 hours after the treatment.

D. In Vivo Mouse Treatment

A total of 15 animals were randomized to receive daily injections with 5 mg/kg Beta-CD-3BrPA (in a 1:1 ratio) (N=10) or vehicle control (N=5). Baseline bioluminescence imaging confirmed tumor growth in all animals (five representative animals shown in FIGS. 4 and 5). After two weeks of intra-peritoneal injections, all animals were subjected to follow-up imaging. Animals treated with the vehicle demonstrated a strong increase of the bioluminescence signal, representing tumor progression.

Male athymic nude mice (20-25 g, 4 weeks old, Crl:Nu-Nu, Charles River Laboratories, Wilmington, Mass., USA) were used in accordance with the institutional guidelines under approved protocols. Mice were maintained in laminar flow rooms at constant temperature and humidity with food and water given ad libitum. The MiaPaCa-2 cell line, stably transfected with the luciferase-aminoglycoside phosphotransferase fusion gene under the control of the elongation factor 1 alpha promoter was used. Mice were anesthetized by isoflurane inhalation anesthesia before surgery and treatment. A small left abdominal flank incision was made and the pancreas was exteriorized. Orthotopic pancreatic tumors were generated by injection of 1-2×10$^6$ MiaPaCa-2 cells into the tail of the pancreas. A successful subcapsular intrapancreatic injection of the tumor cells was identified by the appearance of a fluid bleb without intraperitoneal leakage.

For bioluminescence imaging (BLI), anesthetized mice bearing orthotopic tumors were injected intraperitoneally with 150 mg/kg of D-Luciferin (Gold Biotechnilogy, St Louis, Mo., USA) and optically imaged after 5 mins. using the IVIS 100 (Xenogen Corp, Alameda, Calif., USA). The pseudocolor image which represented the spatial distribution of detected photons was overlaid on a grayscale photographic image. Signal intensity was quantified with ROIs (p/s/cm$^2$/Sr) after a 10-second exposure using Living Image software (Xenogen Corp.). Imaging was performed on day 7, 14, 21, 28 and 35 after tumor implantation.

Following the confirmation of tumor growth in each animal using BLI one week after tumor implantation, all animals were randomized in 3 groups to receive either 3-BrPA, CD-3BrPA or the vehicle via daily intra-peritoneal injections (injection volume, 500 µl/mouse/day; dose, 5 mg/kg). The injection solution was prepared by dissolving the chemicals in phosphate buffered saline, adjusted to a pH of 7.4. Animals were observed once per hour during the initial injections and every 4-6 hours after every follow-up injection. Any changes in the overall clinical condition were noted for all treatment groups.

Within 24 hours after the last BLI imaging, animals were sacrificed using cervical dislocation. The entire abdomen was opened and tumors were obtained using en-bloc extraction with the spleen and pancreas. Tumor specimens were fixed using 4% paraformaldehyde for 72 hours, paraffin embedded, and sectioned. Histological sections were hematoxylin and eosin (H&E) stained and interpreted in consultation with a pathologist.

Example 2: In Vitro Effects of Cyclodextrins Encapsulating 3-BrPA on Human Pancreatic Cancer Cell Lines Two cell lines of human pancreatic cancer, namely MiapaCa-2 and Suit-2, were tested for their response to 3-BrPA and CD-3-BrPA. MiaPaCa-2 is derived from a locally invasive human adenocarcinoma and forms typical solid nodules within the pancreas. It is known to show a pronounced resistance to several standard-of-care anticancer agents, including gemcitabine. Suit-2 is derived from a highly aggressive pancreatic tumor that has been isolated from a metastatic liver mass. It has highly aggressive phenotypic properties, such as invasion and migration. The cellular response or the cell viability was assayed using the standard ATP viability assay. Each experiment was repeated at least twice, with triplicate biological samples.

Figure 2:
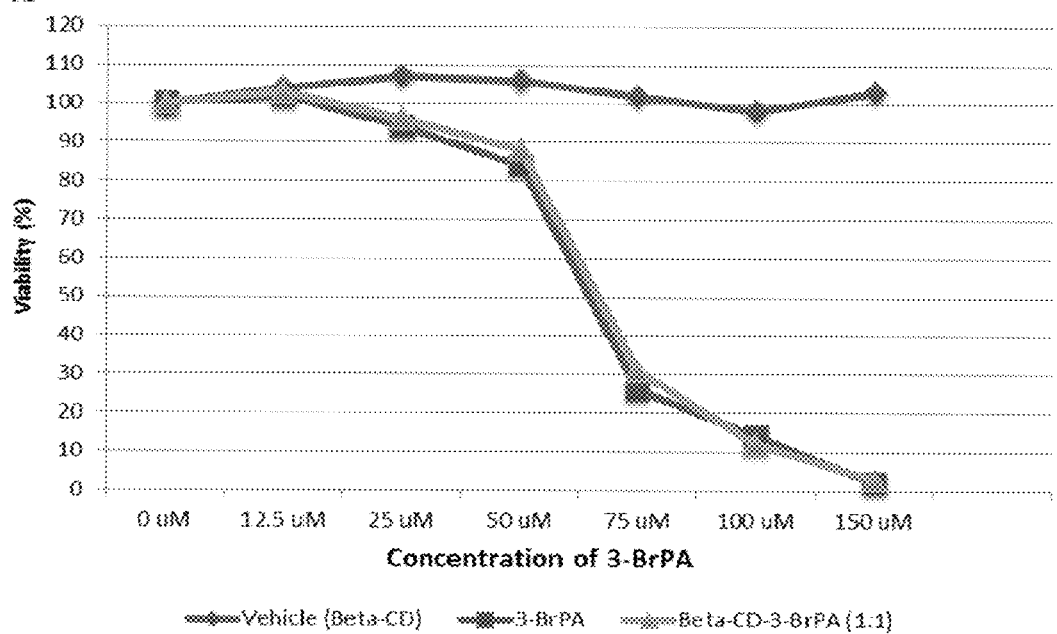
FIG. 2 includes two panels, A and B, and shows the effects of 3-BrPA or Beta-CD-3-BrPA on MiaPaCa2 cells (Panel A) and Suit-2 cells (Panel B) after 24 hours of treatment.
Figure 2:
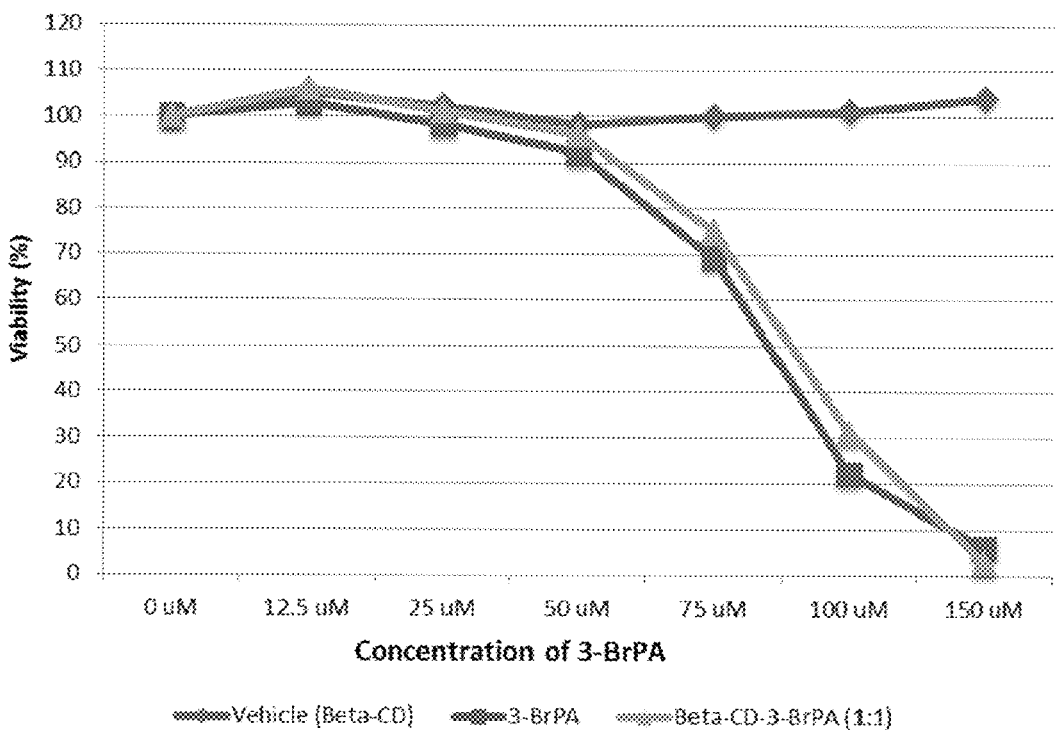

FIG. 2 (Panels A and B) show the effects of 3-BrPA (conventional 3-BrPA in phosphate-buffered saline without any cyclodextrin encapsulation or complex formation) or beta-CD-3-BrPA (succinyl-β-cyclodextrins encapsulating 3-BrPA in phosphate-buffered saline) on MiaPaCa-2 cells (Panel A) and Suit-2 cells (Panel B) after 24 hours of treatment. The data show a dose dependent decrease in viability of cells treated with beta-CD-3-BrPA compared to 3-BrPA treated cells. In addition, the multi-drug resistant MiaPaCa2 cells were found to be more sensitive to 3-BrPA/ CD-3-BrPA than Suit2 cells. The vehicle (β-cyclodextrin in phosphate-buffered saline without any 3-BrPA) by itself did not contribute to any toxicity.

Figure 3:
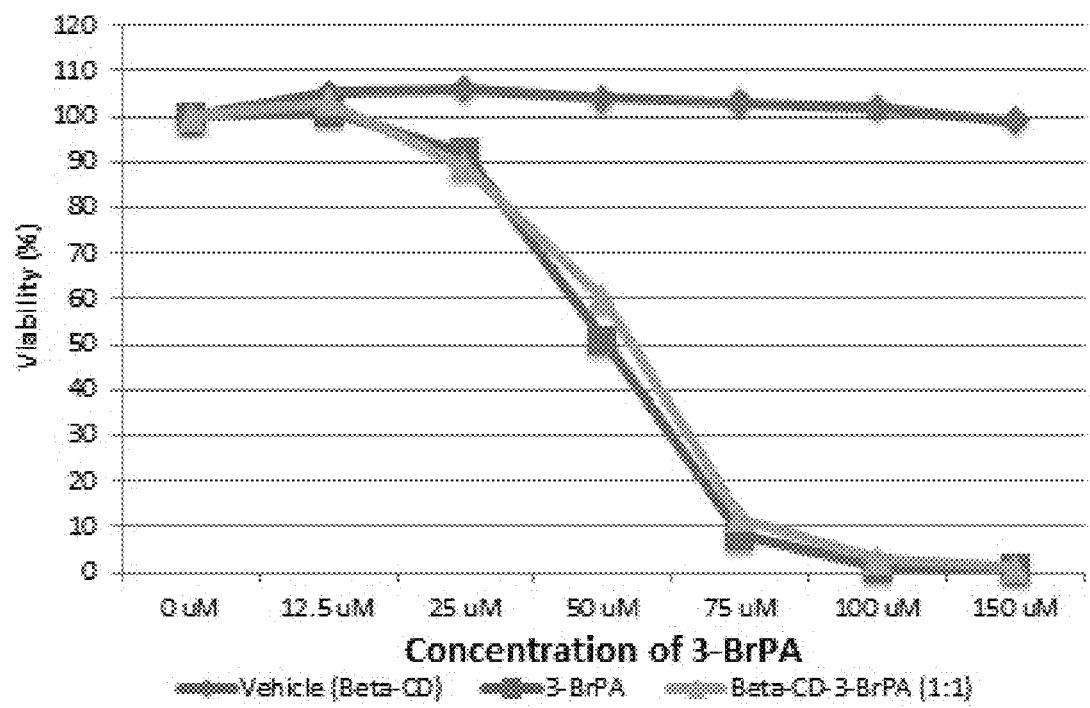
FIG. 3 shows the effects of 3-BrPA or Beta-CD-3-BrPA on MiaPaCa2 cells after 72 hours of treatment.

FIG. 3 shows the effects of 3-BrPA (conventional 3-BrPA in phosphate-buffered saline without any cyclodextrin encapsulation or complex formation) or beta-CD-3-BrPA (succinyl-β-cyclodextrins encapsulating BrPA in phosphate-buffered saline) on MiaPaCa2 cells after 72 hours of treatment. MiaPaCa-2 cells show a significant loss of viability even at ~50 uM concentration of CD-3-BrPA at 72 hours of treatment, whereas at the same concentration at 24 hours (Panel A), there was no significant loss of viability. Thus, with longer duration (48 hrs.) of treatment, CD-3-BrPA at fairly low concentration (50 uM) is sufficient to initiate cell death (~50% death) (FIG. 3).

Example 3: Materials and In Vivo Effects of Cyclodextrins Encapsulating 3-BrPA in a Mouse Model of Human Pancreatic Cancer An athymic mouse model of human pancreatic cancer was used for in vivo studies. The human pancreatic cancer cell line, MiaPaca-2, stably expressing the luciferase gene, was orthotopically implanted onto the pancreas. Tumor growth and response were monitored by bioluminescence imaging.

Table 1 describes the clinical signs or symptoms observed in tumor-bearing animals treated with a high-dose of 3-BrPA or CD-3-BrPA. These symptoms were recorded in an unbiased and blind-study fashion. These symptoms were observed at a dose of >5 mg/kg body weight and at a concentration of ~3.5 mM (higher than the recommended therapeutic dose). Undesirable clinical signs or symptoms were seen in the mice treated with 3-BrPA and these signs or symptoms were significantly less in the mice treated with CD-3-BrPA, indicating that the cyclodextrin carrier protects the subject from the side effects of the 3-BrPA molecule.

TABLE 1

| Clinical Signs/Conditions | 3-BrPA treatment | Succinyl-β-cyclodextrins-3-BrPA treatment |
|---|---|---|
| Seizures/Shiver/Spasms | +++ | +/− |
| Salivation | +++ | +/− |
| Shortness of Breath | +++ | +/− |
| Abnormal Behavior (e.g., inactive/unresponsive) | +++ | +/− |
| Hypothermia | +++ | +/− |

Figure 4:
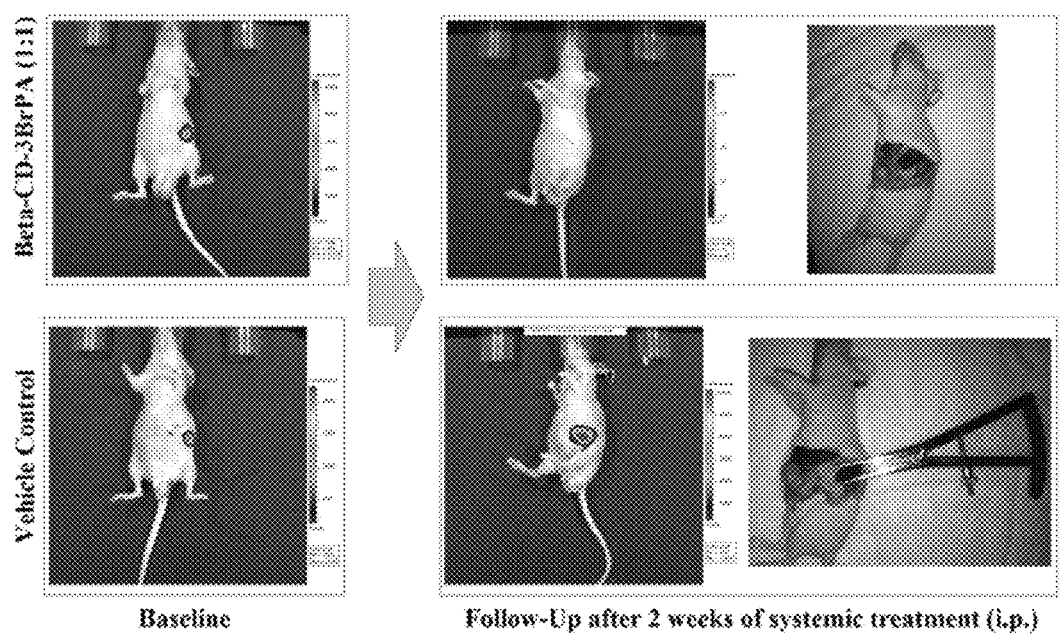
FIG. 4 shows the effects of Beta-CD-3-BrPA on in vivo tumor growth.
Figure 5:
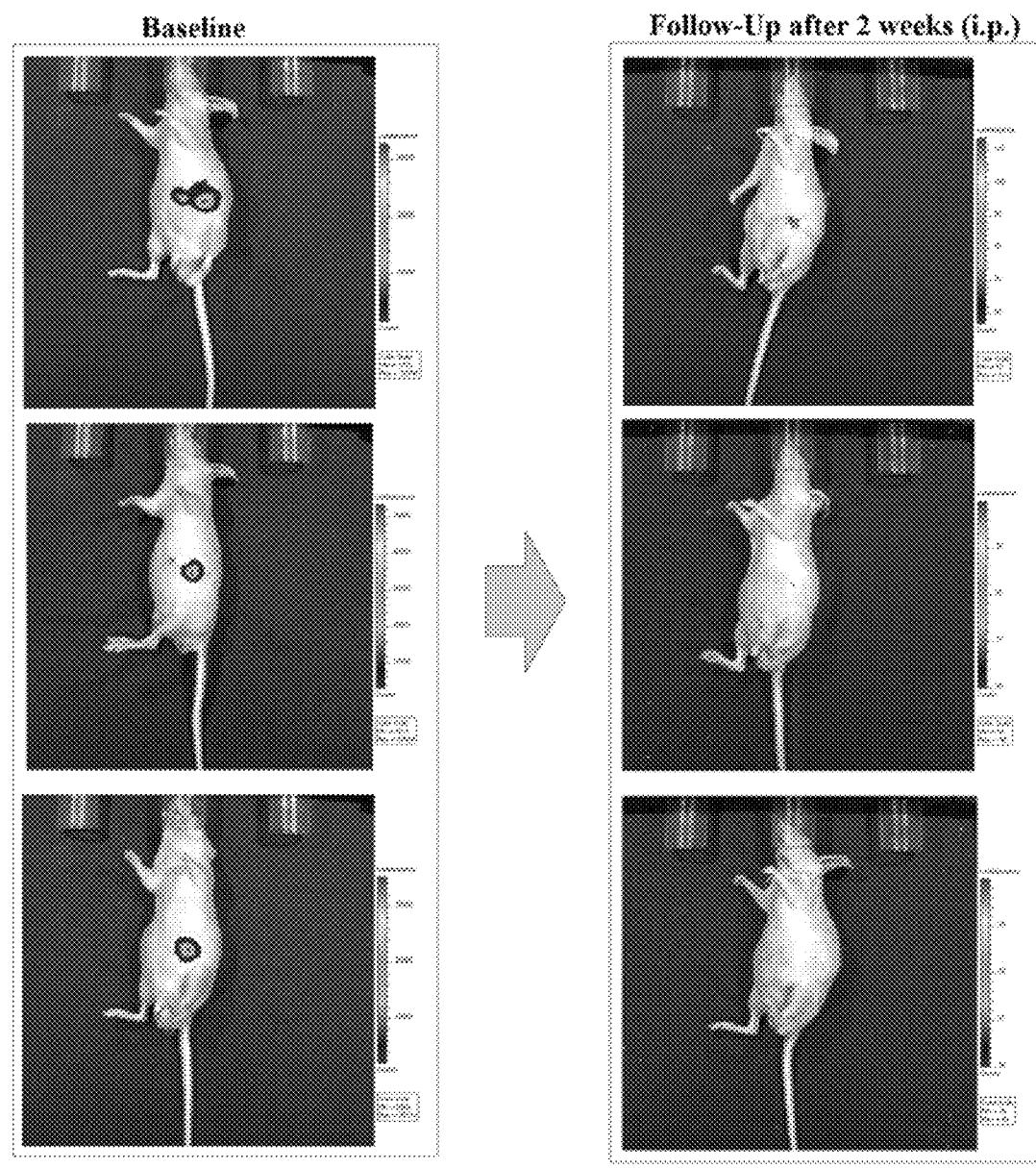
FIG. 5 shows complete tumor response in 3 mice treated with Beta-CD-3-BrPA.

Animals treated with succinyl-β-cyclodextrin-3-BrPA showed complete or almost-complete tumor response on bioluminescence imaging (FIGS. 4 and 5). Subsequently, animals were sacrificed to confirm the bioluminescence results with necropsy (FIG. 4). The results indicate that CD-3BrPA preserves its anticancer activity even after complex formation with CD.

Figure 6:
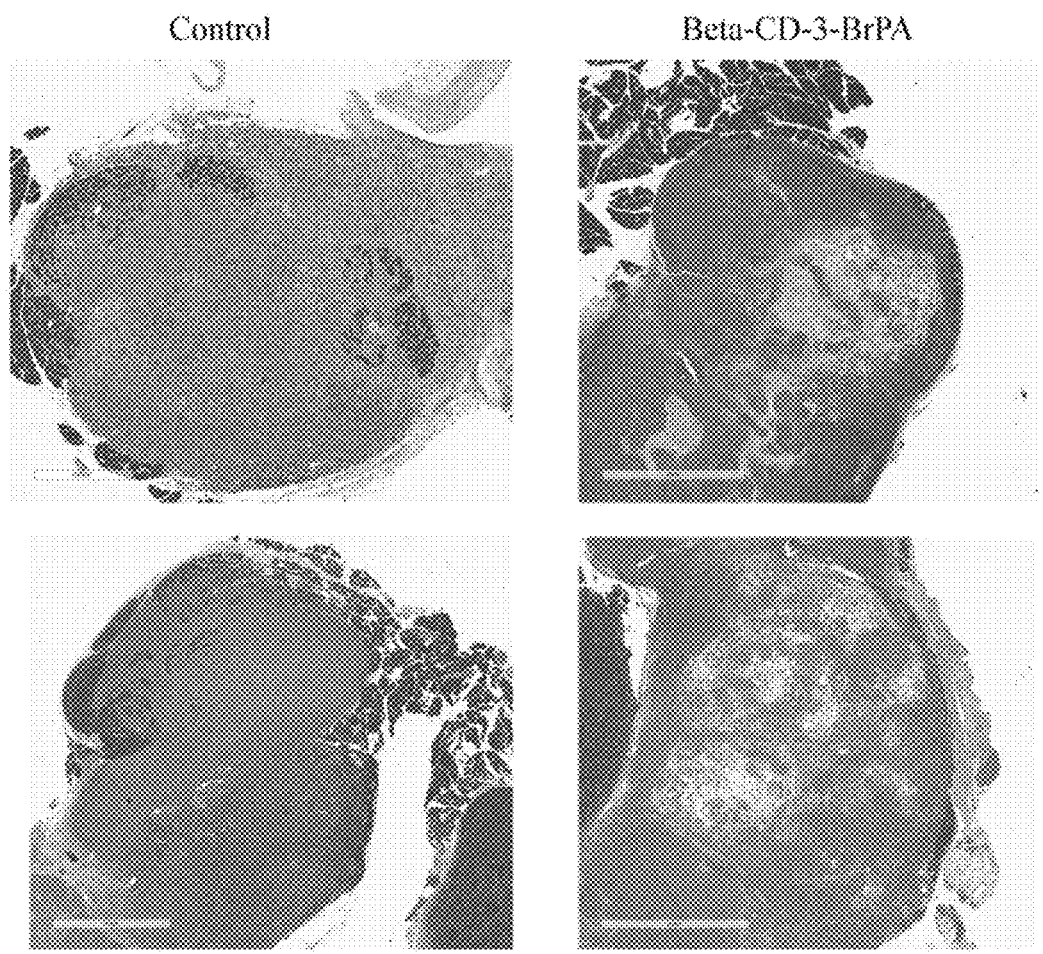
FIG. 6 shows the results of histopathological analysis of the orthotopic MiaPaCa-2 tumors treated as in FIGS. 4 and 5.

Histopathological analysis of the orthotopic MiaPaCa-2 tumors was performed. FIG. 6 shows that hematoxylin and eosin (H&E)-stained tumors showed no changes in the control group, while tumors harvested from treated animals show extensive central necrosis as well as areas of dissociating tumor tissue.

Thus, it has been determined that cyclodextrin complex formation does not affect the anticancer properties of 3-BrPA, as evident from both in vitro and in vivo data. Also, the activity of 3-BrPA can be preserved or protected by CD until it is delivered or distributed to the target organ or tumor. In addition, CD-3-BrPA administration to animals results in lesser toxicity or related-clinical signs compared to 3-BrPA alone.

Example 4: Materials and Methods for Examples 5-6

The experiments described in Examples 2-3 were expanded in order to advance the results obtained therefrom using the following materials and methods. For example, pancreatic ductal adenocarcinomas (PDAC) rank as the fourth most common cause for cancer related death in the world (Siegel et al. (2014) *CA Canc. J. Clin.* 64:9-29). As the majority of patients are diagnosed at advanced stages, therapeutic options remain limited and the prognosis is dismal with a 5-year survival rate of less than 5% (Hidalgo (2010) *New Engl. J. Med.* 362:1605-1617). The last two decades brought significant advances in the understanding of tumorigenesis and disease progression in pancreatic cancer, which can now be seen as a diverse and multifactorial neoplastic process (Hidalgo (2010) *New Engl. J. Med.* 362:1605-1617; Hanahan and Weinberg (2011) *Cell* 144: 646-674). Pancreatic tumor tissue is composed of several distinctive, cellular and non-cellular elements including a collagen-rich, poorly vascularized and highly hypoxic, non-neoplastic stroma (Chu et al. (2007) *J. Cell. Biochem.* 101:887-907; Mahadevan and Von Hoff (207) *Mol. Canc. Therapeut.* 6:1186-1197). These characteristics are associated with profound chemoresistance to the most commonly used systemically applicable anti-cancer agents, such as gemcitabine (Muerkoster et al. (2004) *Cancer Res.* 64:1331-1337; Yokoi and Fidler (2004) *Clin. Canc. Res.* 10:2299-2306). Notably, altered energy metabolism has been recently added to the organizing principles of tumor microenvironment and can now be seen as a "hallmark" of pancreatic cancer (Hanahan and Weinberg (2011) *Cell* 144:646-674; Guillaumond et al. (2014) *Arch. Biochem. Biophys* 545:69-73. The oxygen-independent reliance on glycolysis as the main axis of energy supply for cancer cells has long been known as the "Warburg effect"; however, this circumstance has not yet been clinically exploited for therapeutic purposes (Warburg et al. (1927) *J. Gen. Physiol.* 8:519-530; Ganapathy-Kanniappan and Geschwind (2013) *Mol. Cancer* 12:152). 3-bromopyruvate (3-BrPA), a highly potent small-molecular inhibitor of the enzyme glyceraldehyde-3-phosphate dehydrogenase (GAPDH), is the only available anti-glycolytic drug candidate that is able to enter cancer cells selectively through the monocarboxylate transporter 1 (MCT1) (Ganapathy-Kanniappan et al. (2009) *Anticancer Res.* 29:4909-4918; Birsoy et al. (2013) *Nature Genet.* 45:104-108). The anti-tumoral effects of 3-BrPA have been extensively studied and confirmed in several murine tumor models in the setting of loco-regional therapy, delivered either through tumor-feeding arteries or with direct intra-tumoral injections (Ota et al. (2013) *Target. Oncol.* 8:145-151; Geschwind et al. (2002) *Canc. Res.* 62:3909-3913). However, due to its alkylating properties, 3-BrPA has demonstrated significant toxicity when delivered systemically in therapeutic doses, which in return could impede the clinical development and use of this drug in cancer patients (Chang et al. (2007) *Acad. Radial.* 14:85-92; Cao et al. (2008) *Clin. Canc. Res.* 14:1831-1839).

A. Antibodies, Reagents, and Kits

The following primary antibodies were used: rabbit anti-MMP-9 polyclonal antibody (pAB) #3852 (Cell Signaling), DAPI #D1306 (Invitrogen), Alexa Fluor 568 Phalloidin #12380 (Life Technologies), GAPDH (14C10) monoclonal AB (mAB) Alexa Fluor 488 Conjugate #3906 (Cell Signaling), GAPDH pAB #sc-47724 (Santa Cruz), cleaved caspase-3 pAB #9661 (Cell Signaling), MCT-1 pAB #sc50324 (Santa Cruz), and a Ki-67 kit/antibody (Dako Inc.). The following secondary antibodies were used: goat anti-rabbit IgG HRP-conjugated #7074 (Santa Cruz), anti-rabbit IgG (H+L), F(ab')$_2$ fragment PE conjugate #8885 (Cell Signaling), and goat anti-mouse IgG-FITC #sc2010. The following chemicals were used: 3-bromopyruvatic acid (3-BrPA, Sigma Aldrich), gemcitabine hydrochloride salt (LC Laboratories), succinyl-β-cyclodextrin (β-CD, Sigma Aldrich), and D-luciferin potassium salt (Gold Biotechnology, St Louis, Mo., USA). The following cell culture reagents were used: RPMI-1640 (Life Technologies), MEM (Life Technologies), fetal bovine serum (FBS, Thermo Scientific), penicillin/streptomycin (Sigma Aldrich), collagen I rat tail (BD Biosciences, #354326), and controlled atmosphere chamber (Plas. Labs). The following invasion assay reagents were used: matrigel basement membrane matrix (BD Biosciences) and matrigel invasion chamber transwell polycarbonate membrane inserts (Corning). The following kits were used: CellTiter-Glo luminescence cell viability assay kit (Promega), dual-luciferase reporter assay kit (Promega), 2D quant kit (GE Healthcare), histostain plus 3rd gen ICH detection kit (Invitrogen), and diff quik stain kit (Polysciences Inc.). The following imaging equipment was used: Zeiss 700 LSM confocal microscope, Olympus IX81 inverted microscope, Eclipse TS100 inverted microscope (Nikon), and IVIS200 (Xenogen Corp., Alameda, Calif.)

B. Complex Preparation and Nuclear Magnetic Resonance (NMR) Spectroscopy

Figure 7:
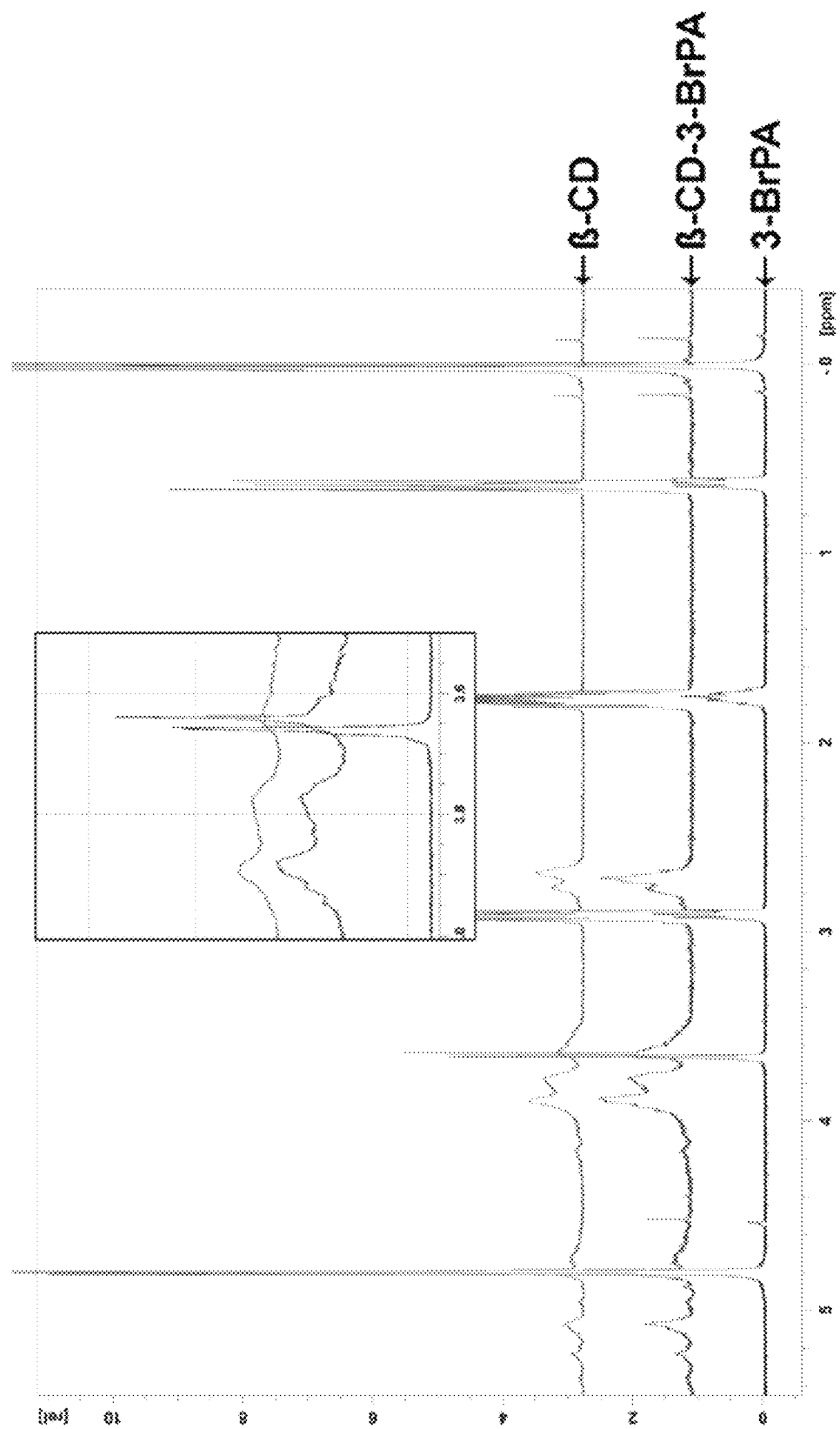
FIG. 7 shows the results of NMR spectroscopy. The magnified insert demonstrates the upheld shift of the methylene protons (0.1 ppm), which was observed upon complexation of β-CD-3-BrPA.

To prepare 3-BrPA encapsulated in β-CD, 3-BrPA (166 mg, 1 mM) was added in small portions (10 mg each) to a stirring solution of β-CD (918 mg in 20 ml DI water). After completing the addition, the solution was sonicated for 1 hour at 50° C. The sonicated solution was then allowed to shake overnight on a thermomixer at 25° C., flash frozen in a dry ice-acetone bath and lyophilized. The lyophilized complex was used as such for further biological and biophysical studies. $^1$H NMR experiments were performed at 400 MHz on a Bruker Avance spectrometer. The NMR spectra were recorded in 99.9% $D_2O$ and are reported in parts per million downfield relative to tetramethysilance (TMS). Ten mM solutions of β-CD alone, 3-BrPA alone, or the complex of 3-BrPA and β-CD, were prepared with 1% DSS (3-(trimethylsilyl)-1-propanesulfonic acid, sodium salt; Sigma Aldrich) as an internal standard. Spectra were recorded at 25° C. with 32 scans. An upheld shift of the methylene protons (0.1 ppm) was observed upon complexation (see FIG. 7).

C. Monolayer Cell Culture and Viability Assay

Two human pancreatic adenocarcinoma cell lines, lucMiaPaCa-2 (stably transfected with the luciferase-aminoglycoside phosphotransferase fusion gene, kindly provided by Dr. Phuoc T. Tran) and Suit-2 (kindly provided by Dr. Shinichi Ota, Japan) were cultured in RPMI or MEM media, respectively, both supplemented with 10% FBS and 1% Penicillin-Streptomycin. The effects of different drugs on cell viability were determined by quantifying intracellular adenosine triphosphate (ATP) levels using a luminescence-based kit (CellTiter-Glo, Promega) and a multilable 96-well plate (Costar). The accuracy and reproducibility of viability measurements using this luminescence-based kit in lucMiaPaCa-2 cells was confirmed using the Dual-Reporter assay kit (Promega). In brief, $5\times10^3$ cells were seeded in triplicate and incubated for 72 hrs. under normoxic or hypoxic (1% $O_2$-level, balanced with $CO_2$ and nitrogen within a controlled atmosphere chamber) conditions. Indicated amounts of free 3-BrPA, 1:1-β-CD-3-BrPA or β-CD as a control were dissolved in PBS and added to the medium for 24 hrs. of treatment. For the experiments with gemcitabine, cells were incubated for 24 hrs. prior to a 72 hrs. exposure to the drug. Cell viability was determined following the manufacturer's protocol.

D. 3D Organotypic Cell Culture, Imaging, and Immunofluorescence

A collagen 1-based 3D organotypic cell culture was used to mimick an extracellular-matrix (ECM)-rich environement and to test the effects of 3-BrPA on tumor invasion (Cheung et al. (2013) *Cell* 155:1639-1651; Nguyen-Ngoc and Ewald (2013) *J. Microscop.* 251:212-223). Specifically, a collagen solution which initially consisted of 25 µl of 10×DMEM and 217 µl of collagen I (3.83 mg/ml) was prepared on ice. The pH value was adjusted by dropwise addition of sodium hydroxide (Sigma Aldrich) to reach pH=7.0.

The collagen I was then diluted using DMEM F12/ GlutaMAX (Life Technologies) to a final concentration of 3 mg/ml. An underlayer was created on the bottom of each well of an uncovered glass-bottom 24-well plate (InVitroScientific) using 15 µl of the collagen solution, which was then allowed to polymerize at 37° C. for at least 1 hr. The remaining collagen solution was kept on ice for 3-5 hrs. to allow initial polymerization. A total of $65\times10^3$ lucMiaPaCa-2 or $45\times10^3$ Suit-2 cells were resuspended in a volume of 150 µl collagen solution. By creating a drop with the height of 0.5 cm, the cell suspension was placed on top of the pre-warmed underlayer. The collagen-cell suspension was allowed to polymerize for 1 h at 37° C. and subsequently covered with cell culture medium (Nguyen-Ngoc and Ewald (2013) *J. Microscop.* 251:212-223).

3D organoids were treated either once or sequentially. For single treatments, embedded cells were incubated for 5 days under normoxic or hypoxic (1% $O_2$-level within a controlled atmosphere chamber) conditions prior to treatment. On day 5, medium was replaced by 1:1-β-CD-3-BrPA/3-BrPA/β-CD-containing medium and the cells were incubated for 24 hrs. with the respective concentrations of the drug. For experiments with gemcitabine, cells were allowed to grow for 48 hrs. before being treated and incubated with the drug for another 72 hrs. Initial experiments with gemcitabine did not demonstrate any efficacy after 24 hrs., and it was decided to follow the most commonly reported incubation times of 72 hrs. Sequential treatment with 3-BrPA was performed on alternate days for one week with the respective doses and evaluated by bright field microscopy (Olympus) at 40× magnification with a 1.3 NA oil objective. A Hamamatsu Photonics C9100-02 EMCCD camera was used to acquire the images with the SlideBook 5.0 program.

Microscopic observations were compared with the quantification of cell viability as seen on in vitro bioluminescence imaging (BLI). For the latter measurements, the cell culture medium covering the 3D organotypic cell culture was replaced by 500 ul of a luciferase substrate (D-luciferin, potassium salt, Life Technologies, 20 mg/ml) in PBS. After 5 mins of exposure, the plate was positioned and images were acquired (Xenogen Ivis Imaging System 100). Signal intensity was determined by the photon emission (in counts) and measured within a region of interest (ROI) which enclosed the entire 3D organoids (Living Image Software, PerkinElmer).

The microscopic and BLI findings were verified using immunofluorescence microscopy. 3D organoids were fixed using 4% formaldehyde and cryofixed with OCT Compound (Tissue Tek) at −80° C. The samples were cut into sections of 100 µm thickness at −20° C. OCT was washed off using PBS twice for 10 mins Each. Prior to staining, sections were permeabilized with 0.5% Trizol 100 in PBS for 30 mins and washed twice with PBS for 10 mins each. After blocking with 10% FBS in PBS for 2 hrs., samples were incubated with primary antibodies (Alexa Fluor 568 Phalloidin, Invitrogen, 1:100; GAPDH Alexa Fluor 488 conjugate, Cell Signalling, 1:800; cleaved caspase-3, Cell Signalling, 1:500; HIF-1 alpha 1:50) for 1 hr. at room temperature (RT) under light protection. For non-conjugated primary antibodies, additional incubation with a phycoerythrin (PE)- or fluoresceine isothiocyanate (FITC)-conjugated secondary antibody for 1 hr. at RT was used. This was followed by two washings with PBS for 10 mins. each. DAPI was used as a counter stain at a concentration of 300 ng/ml and added to the specimen simultaneously with the conjugated antibody. Specimens were sealed with an antifading mountant and covered with a coverslip. Confocal fluorescence microscopy was performed at 40× magnification with a 1.4 NA oil objective and 63× with a 1.4 NA oil objective. Images were analyzed with Zen2012 software (Carl Zeiss). Excitation and emission wavelengths were those recommended by the conjugate manufacturers. For example, 555 nm was used to excite for phalloidin and PE-conjugates, 488 nm for Alexa Fluor 488, as well as FITC-conjugates and 405 nm for DAPI. Emission was detected between 555 and 1000 nm for red fluorescence and 490 nm and above for green fluorescence. Emission of DAPI was captured below 490 nm or below 529 nm when imaged with red or green fluorescence, respectively.

E. Matrigel Invasion Assay, Zymography, and Immunoblotting

The ability of 3-BrPA to inhibit tumor invasion was studied using a matrigel invasion assay, as well as gelatin zymography (Hu and Beeton (2010) *J. Visual. Exp.* 45:2445; Scott et al. (2011) *J. Visual. Exp.* 58:e3525). For the matrigel invasion assays, a coating buffer containing 0.01 M Tris and 0.7% sodium chloride was prepared and used to dilute the matrigel basement membrane (BD Biosciences, #356234) to 300 ug/ml. Subsequently, Boyden chambers (Transwell, Corning; 6.5 mm-diameter, 8 um pore size) were coated with 100 µl matrigel solution and stored at 37° C. for 2 hrs. to allow for gelatination. Approximately $7.5\times10^4$ cells were resuspended in 500 µl FBS-free medium and plated into the upper chamber of the insert, which was then placed into a 24-well plate containing 750 of FBS-containing medium. After overnight incubation at 37° C., various amounts of 3-BrPA dissolved in PBS were added to the upper chamber. Fourty-eight hours later, non-invasive cells were removed from the matrigel with a cotton swab. Invaded cells adherent to the bottom side of the permeable insert were fixed and stained with the Diff Quik Stain Kit (Polysciences Inc.). Light microscopy was performed using a colored inverted microscope (Eclipse TS 100) at 4×, 10×, and 20× magnification. Invasion of cells was quantified by measuring the area of stained cells after treatment compared to untreated samples at 10× magnification.

Zymography assays were performed to determine the activity of secreted MMP-9. Accordingly, $4\times10^6$ Suit-2 cells and $2.5\times10^6$ lucMiaPaCa-2 cells were seeded in 75 $cm^2$- flasks and incubated overnight at 37° C. under normoxic conditions. The following day, fresh FBS-free medium containing different concentrations of 3-BrPA was added and cells were incubated for an additional 24 hrs. Subsequently, supernatants were collected, filtered, and the final protein concentrations were determined using the 2D Quant Kit (GE Healthcare). After adjustment for concentration, each sample was loaded onto two 10% gelatin zymography gels (Novex, Invitrogen). Following electrophoresis, proteins in one of the two gels were renaturated and enzymatic digestion was allowed overnight at 37° C. in a developing buffer. The gel was stained with 4 parts 0.1% Coomassie Brilliant Blue in 1 part 100% methanol for 24 hrs. and washed with distilled (DI) water until digested areas were detectable as white bands. Western Blot analysis was performed using the duplicate gel. Proteins were blotted onto a PVDF-Membrane and blocked using 5% skimmed milk in 1×TBS and 0.1% Tween in DI (TBST). Primary anti-MMP antibody (Cell Signaling) was used in a 1:1000 dilution and incubated at 4° C. overnight, followed by an HRP-conjugated secondary antibody (Santa Cruz) incubation for 1 hr. at room temperature. The HRP provided an electrochemiluminescence signal (ECL Kit, GE Healthcare), which was analyzed with ImageJ 1.46r software (Wayne Rasband, National Institute of Health) and used to quantify signal intensity by comparing line integrals.

F. Orthotopic Animal Xenografts

Male athymic nude mice (body weight, 20-25 g; 4 weeks old; Crl:NU (NCr)-Fox1$^{nu}$; Charles River Laboratory, Germantown, Md., USA) were used in accordance with institutional guidelines under approved Animal Care and Use Committee protocols. Mice were maintained in laminar flow rooms at constant temperature and humidity with food and water given ad libitum. Orthotopic xenograft tumors were generated by implantation of $1.5 \times 10^6$ lucMiaPaCa-2, suspended in 50 μl PBS, into the tail of the pancreas in anesthetized mice. To accomplish this, mice were placed into a clean anesthesia induction chamber (oxygen flow rate, 1 liter/minute; isoflurane concentration of 3-4%). Upon loss of the righting reflex, animals were placed on the surgical procedure surface, where a nose cone was used to maintain anesthesia (oxygen flow, 0.8 liters/minute; Isoflurane concentration, 1.5-2%). A small, left abdominal flank incision was made, and the pancreas was exteriorized to inject the cell solution using a 30 G Hamilton syringe. A successful subcapsular intrapancreatic injection was identified by the appearance of a fluid bleb without intraperitoneal leakage. The abdominal cavity was closed with a double-layer of non-absorbable suture material (Kim et al. (2009) *Nat. Protocol.* 4:1670-1680).

G. Bioluminescence Imaging and Ultrasound Imaging

Tumor viability was confirmed via in vivo bioluminescence imaging (BLI) on day 7 after the surgical implantation. Anesthetized tumor-bearing mice were injected intraperitoneally with D-luciferin 150 mg/kg and optically imaged 5 minutes later using the IVIS 200 system (Xenogen). The pseudocolor image representing the spatial distribution of photons was overlaid on a previously acquired grayscale photographic image. A region of interest (ROI) was created to include the optical tumor image. Signal intensity was quantified within the ROI in photons/second/squared centimeter/steradian (p/s/cm2/Sr) after a 10-second exposure using Living Image software (Xenogen). Additionally, orthotopic growth of the tumors was confirmed prior to treatment using small-animal ultrasound imaging (USI). In brief, anesthetized mice were subjected to examination using the VEVO2100 (Visual Sonics Inc., Toronto, Canada, kindly provided by Dr. Harry C. Dietz) by applying a MS-550D MicroScan transducer probe with 40 MHz (broadband with 22-55 MHz). Tumor localization was confirmed using the cranial tip of the left kidney and the caudal tip of the spleen as anatomic landmarks (Ota et al. (2013) *Target. Oncol.* 8:145-151; Tuli et al. (2012) *Translat. Oncol.* 5:77-84).

H. Treatment Regimen and Imaging Follow-Up

Animals with tumors, as confirmed by both LI and USI, were randomized into four groups: group 1 (N=21 animals) received daily intraperitoneal injections of the β-CD-3-BrPA complex (in a 1:1 molecular ratio, 5 mg/kg 3-BrPA in 26 mg/kg β-CD, dissolved in 500 μl saline), group 2 (N=7 animals) received intraperitoneal injections of gemcitabine (150 mg/kg dissolved in 200 μl saline, three injections/week as commonly reported in literaure, such as Liau and Whang (2008) *Clin. Canc. Res.* 14:1470-1477; Larbouret et al. (2010) *Annal. Oncol.* 21:98-103), group 3 (N=7) received daily intraperitoneal injections of β-CD (26 mg/kg β-CD, dissolved in 500 μl saline), and group 4 (N=7 animals) received daily intraperitoneal injections of 3-BrPA alone (5 mg/kg dissolved in 500 μl saline). All animals were treated without interruptions for a period of four weeks. BLI was acquired on day 7, 14, 21, 28 after the first injection. Animals were sacrificed on day 28 after the last imaging session or when moribund.

I. Immunohistochemistry

Upon sacrificing the animals, tumors were obtained, fixed with a 4% formaldehyde solution for a period of at least 72 hrs., and embedded in paraffin for immunohistochemical analysis. Hematoxylin and eosin (H&E) staining of the slides was performed according to standard protocols, such as those described in Casadonte and Caprioli (2011) *Nat. Protocol.* 6:1695-1709. Eighteen μm thick tumor sections were stained for the following targets: GAPDH, MCT-1, cleaved caspase-3, and Ki-67 using the Histostain Plus 3rd Gen IHC Detection Kit (Invitrogen), as well as the Ki-67 kit (Dako Inc.). Specifically, specimens were deparaffinized using xylene and rehydrated using a descending ethanol dilution series. After washing with deionized water, samples were permeabilized in boiling retrieval solution containing citrate (Dako) for 40 mins. at 95°. Specimens were cooled down to RT and incubated with 2 drops (~100 ul total) of peroxidase quenching solution for 5 min. and blocked for 20 mins. Incubation with primary antibodies (GAPDH, 1:500; MCT-1, 1:250; Ki-67 and HIF-1α; 1:50, cleaved caspase-3, 1:1,500; in PBS) occured at RT in a moist chamber for 60 mins Biotinylated secondary antibody and streptavidin-peroxidase conjugate were added to the samples in sequence for 10 min. each. 26.5 ul of 3,3'-diaminobenzidine (DAB) chromogen were mixed well with 1 ml of DAB subtrate buffer and 100 ul were added to each specimen for 5 mins. Hematoxylin was used as a counterstain. Incubation steps were followed by washing with destilled water and twice PBS for 2 mins each. Samples were sealed using antifading mountant and covered with a coverslip. All slides were scanned and digitalized at a 20× magnification using a high-resolution Aperio® scanner system (Vista, Calif., USA). The digitalized slides were then assessed using the Aperio ImageScope® software. For the Ki-67-stained tissue sections, a total of 5-10 fields were viewed at 10×, and the number of Ki-67-positive cells, as well as the total number of cells were recorded to calculate the Ki-67 labeling index (formula: Index [%]=[number of positive cells/total cell number]×100).

J. Statistical Data Analysis

All experiments were performed independently and repeated at least three times. Data from the experiments were summarized with means±standard error of the mean. Statistical comparisons of data sets were carried out by the Student's t-test as well as the one-way ANOVA test. Reported BLI signal intensities were normalized among the animals and reported as multiples based on the baseline value.

Figure 8:
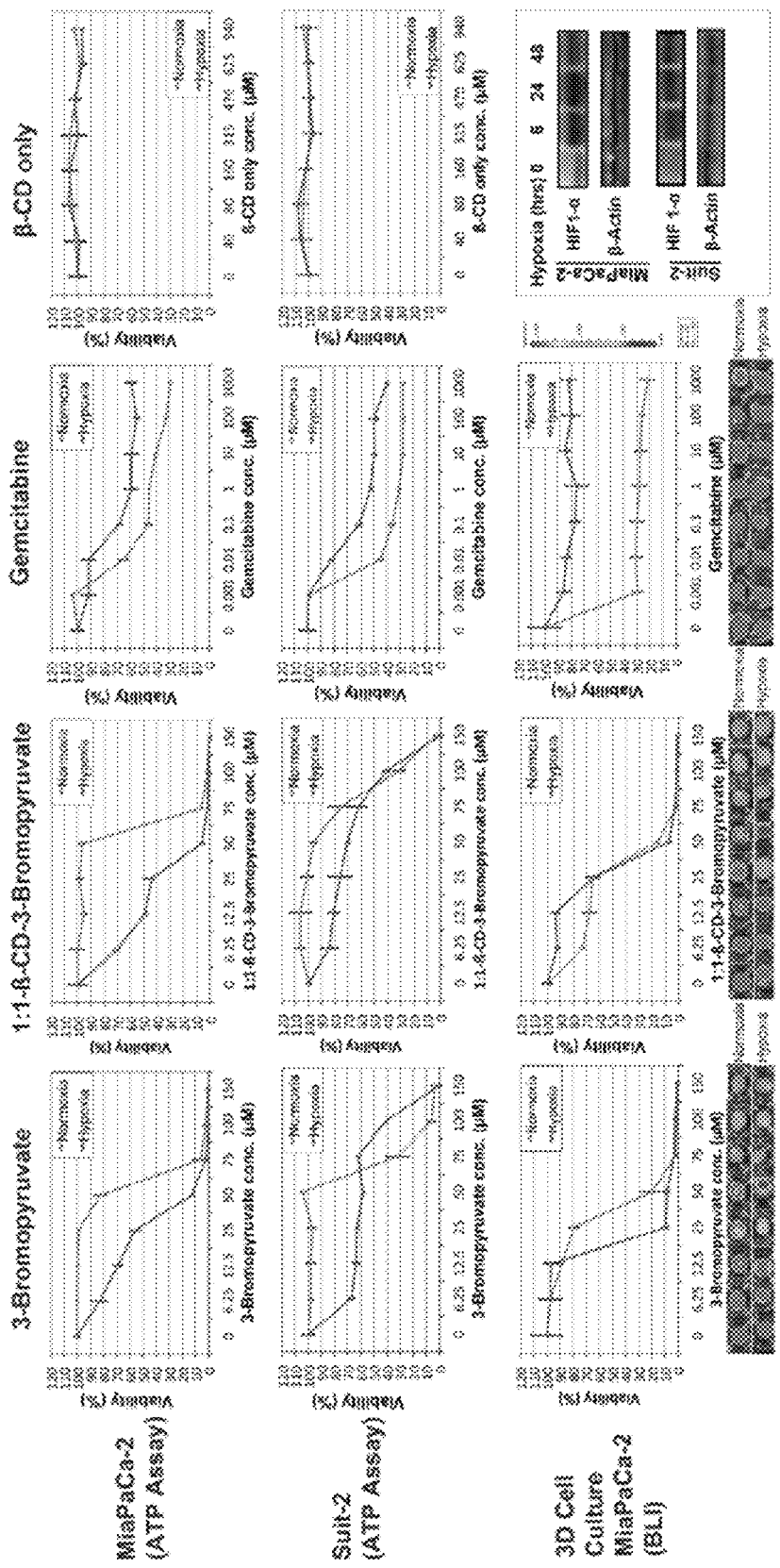
FIG. 8 shows kill curves of 2D and 3D organotypic cell cultures based on the luminescence-based cell viability in MiaPaCa-2 (upper row) and Suit-2 (middle row) cells. Cells were incubated under normoxic and hypoxic conditions for 72 hrs. prior to exposure to 3-bromopyruvate (3-BrPA), 1:1-β-Cyclodextrine (CD)-3-BrPA, or β-CD only as a control, for 24 hrs. Cells were incubated for 24 hrs. before being treated with gemcitabine for 72 hrs. For the 3D organotypic cell cultures (lower row), lucMiaPaCa-2 cells were incubated under normoxic or hypoxic conditions for a total of 6 days. Single-time treatments with 3-BrPA or β-CD-3-BrPA were performed on day 5 for 24 hrs. Exposure to gemcitabine was initiated on day 3 for 72 hrs. Bioluminescence imaging was performed on day 6 to evaluate drug penetration and effects on cell viability. The lower-right box contains the immune-blots for HIF-1alpha to confirm that hypoxia was present.

Example 5: β-CD-3-BrPA Shows Strong Anti-Cancer Effects in 2D and 3D Cell Culture and Targeting Metabolism Reduces Invasive Potential of Cancer Cells Upon NMR-spectroscopic confirmation of the complexation between 3-BrPA and β-CD (FIG. 7), the microencapsulated formulation of the drug was used for further experiments. In order to assess the efficacy of the microencapsulated 3-BrPA (β-CD-3-BrPA) to achieve dose-dependent ATP depletion and cell death, two human pancreatic cancer cell lines were employed. MiaPaCa-2 was derived from a primary pancreatic adenocarcinoma (PDAC) and Suit-2 was derived from a metastatic primary pancreatic adenocarcinoma from a different patient (Kitamura et al. (2000) *Clin. Exp. Metast.* 18:561-571). The dose-dependent effects of β-CD-3-BrPA were compared with free 3-BrPA, as well as gemcitabine, and β-CD was used as a control. As hypoxia is often associated with chemooresistance in PDACs, hypoxic exposure was added to the experimental design (Yokoi and Fidler (2004) *Clin. Canc. Res.* 10:2299-2306; Kasuya et al. (2011) *Oncol. Rep.* 26:1399-1406; Onozuka et al. (2011) *Canc. Sci.* 102:975-982; Zhao et al. (2014) *Canc. Res.* 74:2455-2464)). It was found that β-CD-3-BrPA and free 3-BrPA demonstrated similar cytotoxicity porfiles under normoxic (50-75 µM), as well as hypoxic (12.5-25 µM), conditions and, interestingly, were more sensitive to the drugs when hypoxic (FIG. 8). Cell lines treated with β-CD alone were perfectly viable throughout the experiment, even when exposed to very high confentrations. Similar results were observed for Suit-2 cells but with less pronounced differences between normoxic and hypoxic conditions (FIG. 8). When assessing the efficacy of gemcitabine, $IC_{50}$ in MiaPaCa-2 and Suit-2 cells was barely achieved under normoxic conditions (0.1 µM), no concentration achieved a complete kill, and hypoxia seemed to increase the resistance towards the drug.

Figure 9:
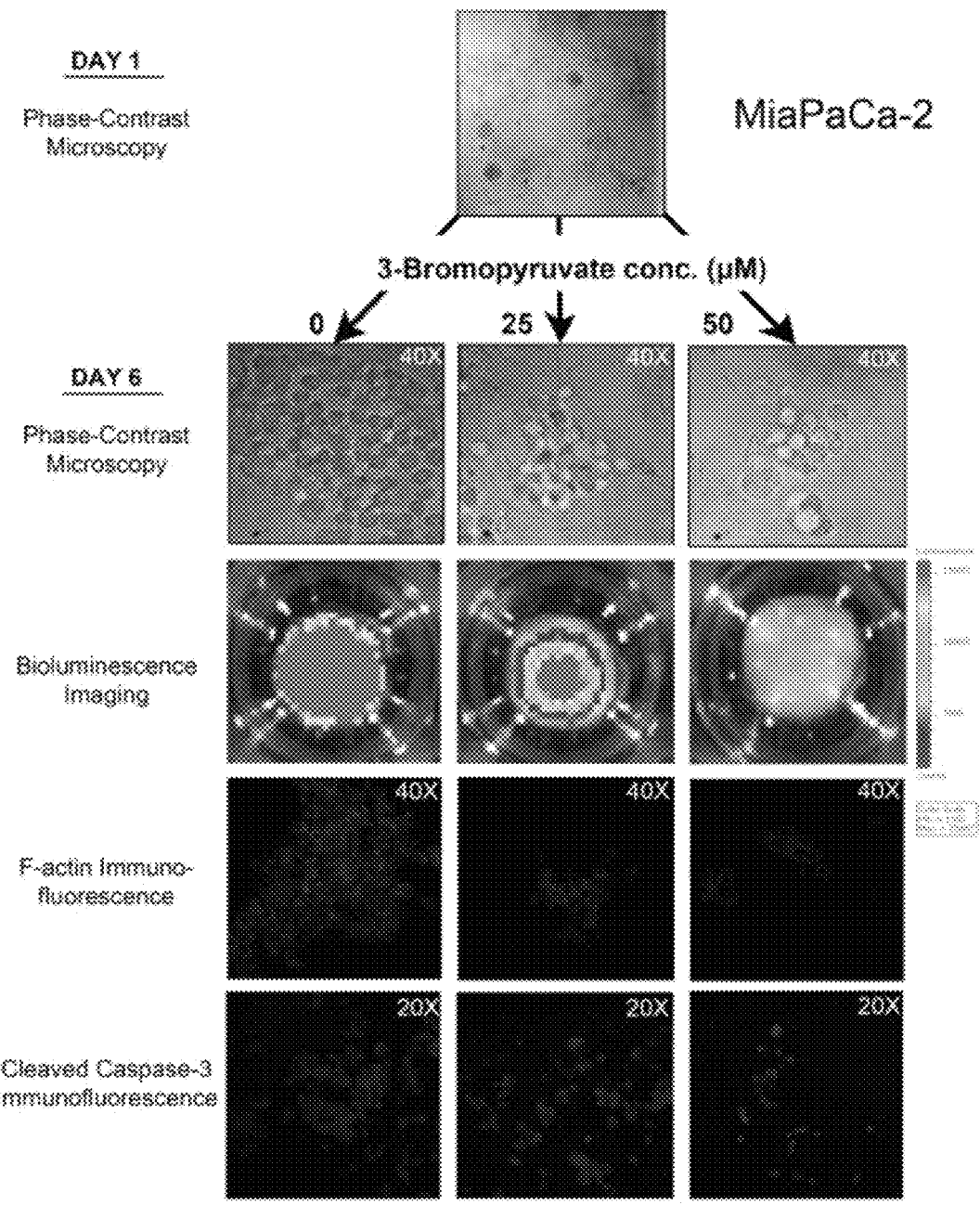
FIG. 9 shows the effects of 3-bromopyruvate in 3D organotypic cell culture. Homogeneous embedding lucMiaPaCa-2 cells into the collagen I-matrix was confirmed by confocal light microscopy (day 1). 3D organotypic cell cultures were incubated under normoxic conditions and treated with 3-BrPA cumulatively three times on alternate days. Phase-contrast microscopy and bioluminescence imaging (the latter only for MiaPaCa-2 cells) were performed on day 6 to evaluate effects on cell morphology and viability. Immunofluorescence staining of F-actin and cleaved caspase-3 were done in cryosections of the 3D organotypic cell culture. DAPI was used as nucleic acid counterstain.
Figure 10:
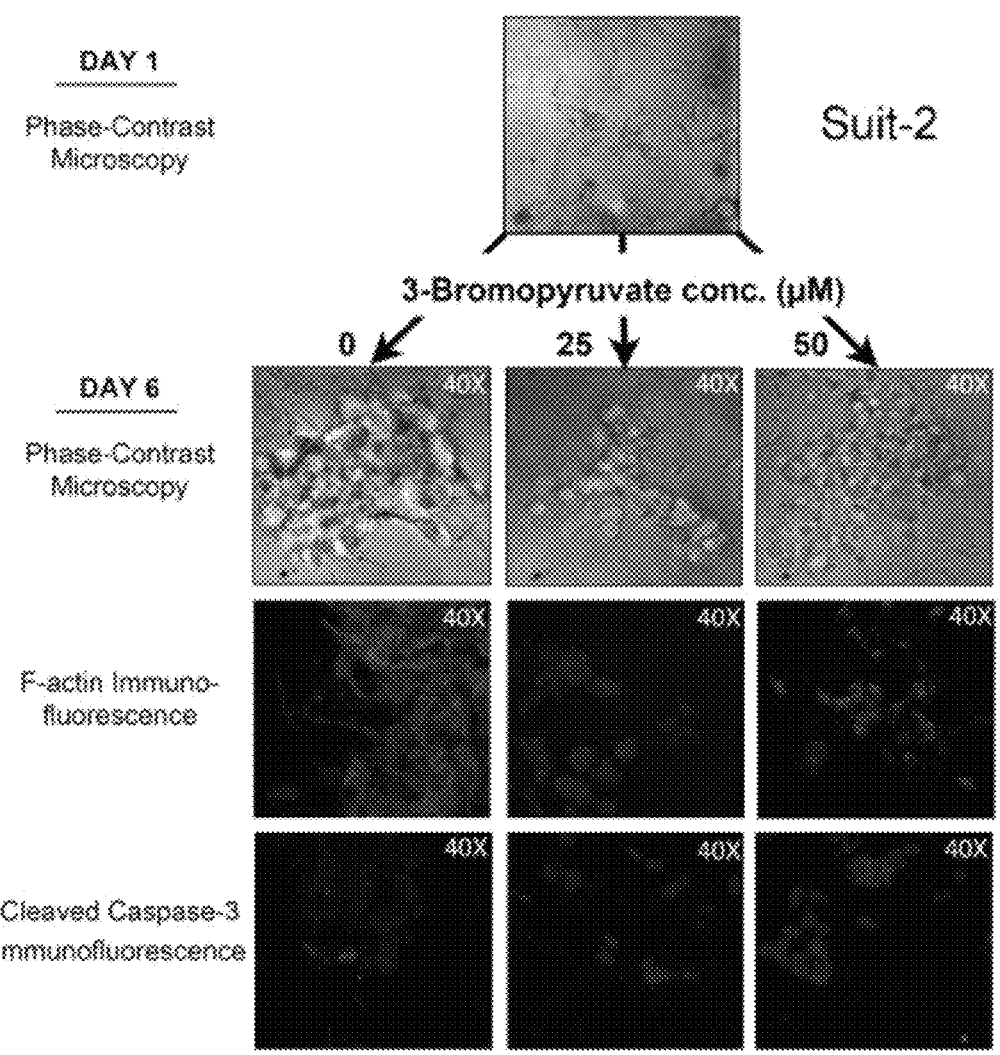
FIG. 10 shows further effects of 3-bromopyruvate in 3D organotypic cell culture. Homogeneous embedding of Suit-2 cells into the collagen I-matrix was confirmed by confocal light microscopy (day 1). 3D organotypic cell cultures were incubated under normoxic conditions and treated with 3-BrPA cumulatively three times on alternate days. Phase-contrast microscopy and bioluminescence imaging (the latter only for MiaPaCa-2 cells) were performed on day 6 to evaluate effects on cell morphology and viability. Immunofluorescence staining of F-actin and cleaved caspase-3 were done in cryosections of the 3D organotypic cell culture. DAPI was used as nucleic acid counterstain.

In order to test the efficacy of β-CD-3-BrPA in an ECM-rich environment, lucMiaPaCa-2 cells were cultured in a 3D Collagen 1 matrix and treated with a single dose of either β-CD-3-BrPA, free 3-BrPA or β-CD (as a control). BLI quantification showed that both drug formulations had equivalent potencies in normoxic conditions ($IC_{50}$, 25-50 µM) (FIG. 8). Under hypoxic conditions, MiaPaCa-2 cells were slightly more sensitive to free 3-BrPA than to β-CD-3-BrPA (FIG. 8). The cells cultured in 3D were treated sequentially with the drugs, as described in Example 4. Morphological, BLI, and immunofluorescence-based analysis confirmed the ability of 3-BrPA to penetrate an ECM-rich matrix and to inhibit cell proliferation, as well as to induce apoptosis (FIGS. 9-10). As such, untreated MiaPaCa-2 cells proliferated and formed "grape"-like structures within the collagen 1 matrix, while Suit-2 cells demonstrated a more invasive growth pattern with cellular protrusions visible after 6 days of growth (FIG. 10). When treated with 3-BrPA, proliferation in both cell lines was inhibited with a marked reduction of cell protrusions in Suit-2 cells (FIG. 10). In addition, immunofluorescence imaging confirmed a dose-dependent induction of apoptosis by 3-BrPA.

Figure 11:
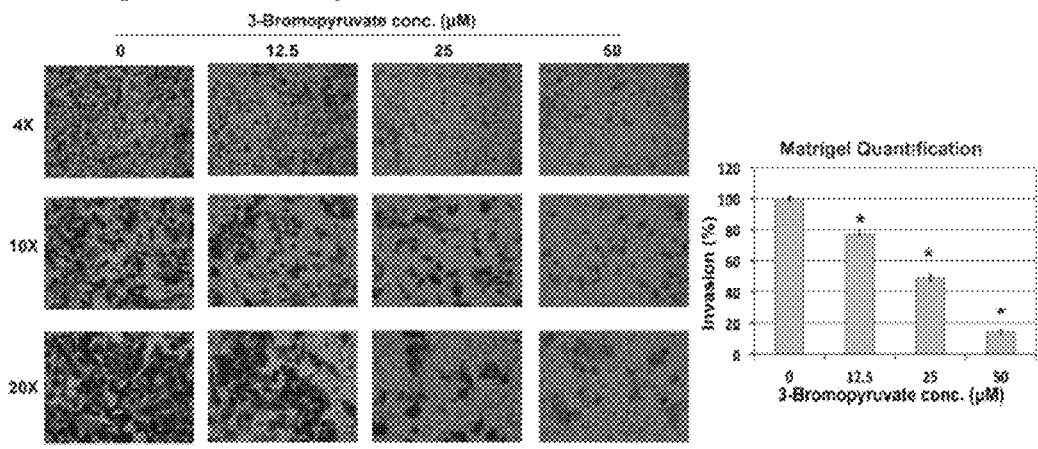
FIG. 11 includes four panels, A to D, and shows the effects of 3-bromopyruvate on cell invasiveness. MiaPaCa-2 (Panel A) and Suit-2 (Panel B) cells were plated into a Boyden invasion chamber. Incubation overnight was followed by treatment with 3-bromopyruvate for 48 hrs. (MiaPaCa-2) or 72 hrs. (Suit-2). Invaded cells on the bottom side of the membrane of the invasion insert were stained using a Giemsa-like staining Images show invaded cells at 4×, 10×, and 20× magnification. Relative quantification of invasion was calculated by measuring the area of stained cells in the entire field of view at 10×. MMP-9 activity and secretion were determined in the concentrated supernatant of MiaPaCa-2 and Suit-2 cells by zymography (Panel C) and Western Blot (Panel D). (*) indicates statistical significant ($p$-value <0.05).
Figure 11:
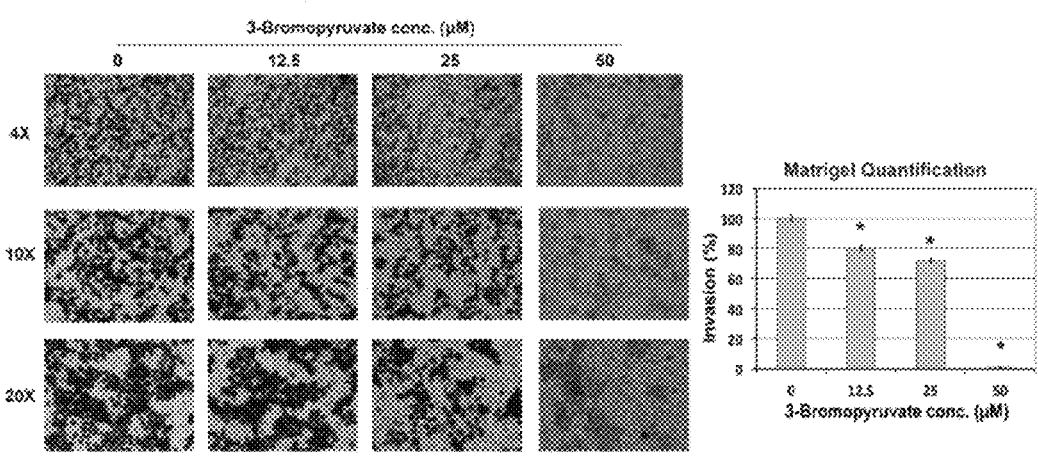
Figure 11:
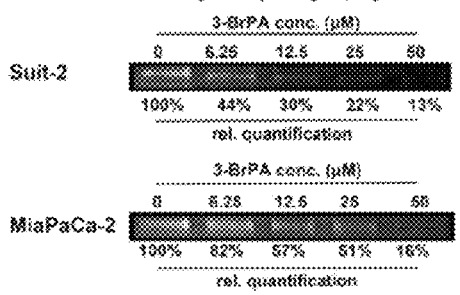
Figure 11:
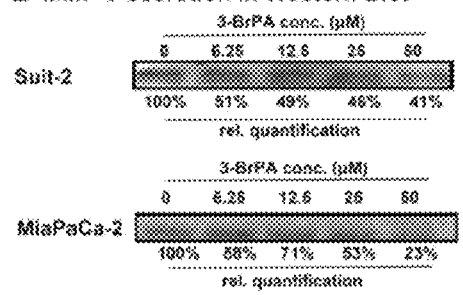

In addition, the ability of 3-BrPA to inhibit the invasiveness of pancreatic cancer cells in sub-lethal drug concentrations was tested using a matrigel invasion assay. As shown in FIG. 11 (Panels A and B), both the locally invasive MiaPaCa-2 cells and the metastatic Suit-2 cells showed a reduction in invasion at drug concentrations as low as 12.5 µM. In addition, the effect of sub-lethal doses of 3-BrPA on the secretion of the matrix-metalloproteinase 9 (MMP-9), a well-described marker for the invasive potential of pancreatic cancer cells, was tested using gelatin zymography and immunoblotting (Jones et al. (1999) *Annal. N. Y. Acad. Sci.* 880:288-307; Merdad et al. (2014) *Anticanc. Res.* 34:1355-1366; Yang et al. (2001) *J. Surg. Res.* 98:33-39). Accordingly, a marked reduction in the secretion of MMP-9 was detected in both cell lines. This effect was observed beginning with a 3-BrPA concentration of 6.25 µM, which is a dose that did not induce apoptosis or reduce cell viability, and an earlier onset in the more metastatic Suit-2 cell line (FIG. 11, Panels C and D).

Figure 12:
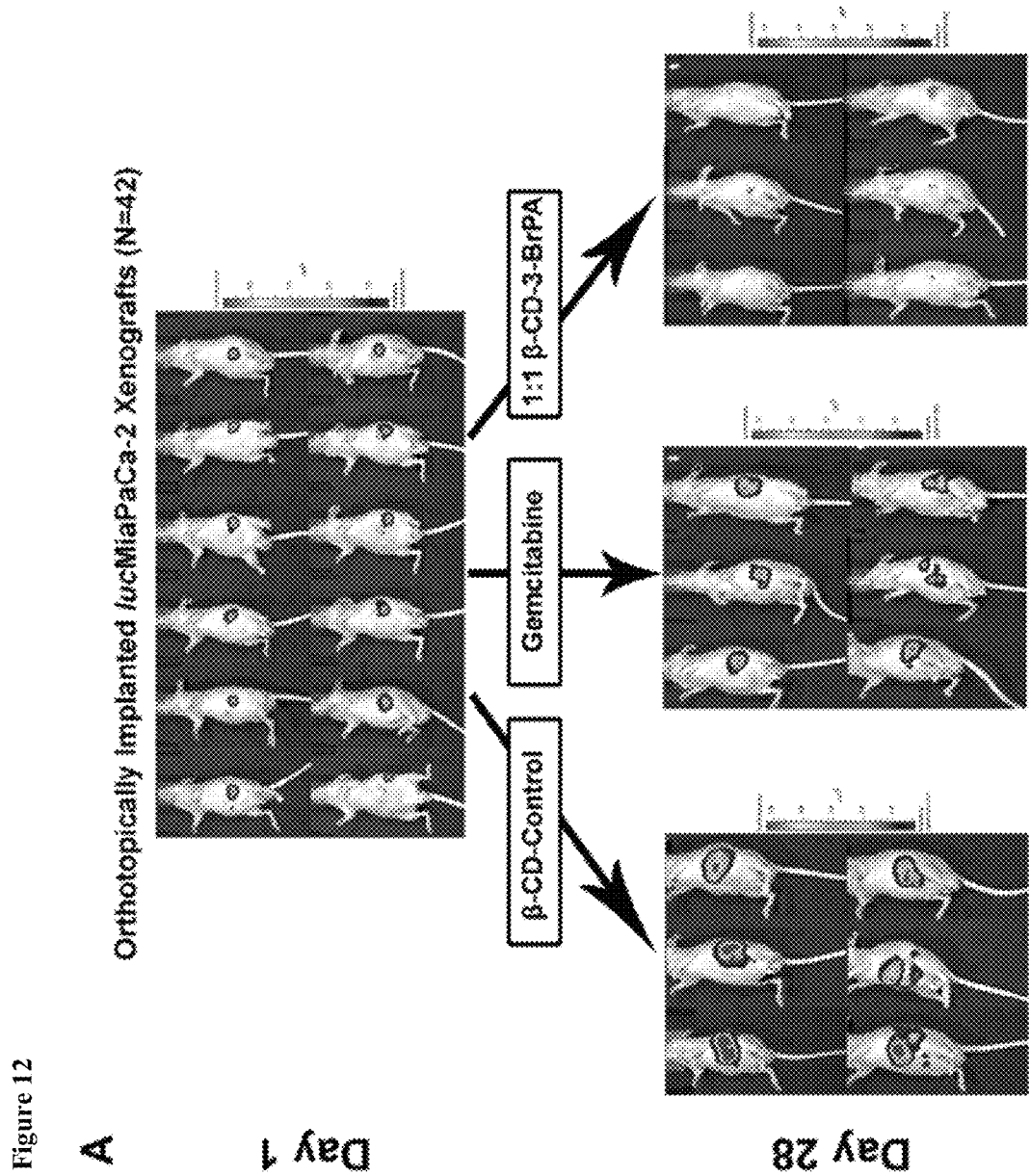
FIG. 12 includes four panels, A to D, and shows the in vivo efficacy of β-cyclodextrin-3-bromopyruvate. A total of 42 male nude mice were orthotopically implanted with a total of 1.5×10⁶ lucMiaPaCa-2 cells. After one week of xenograft growth, tumors were confirmed using bioluminescence imaging (BLI). A representative number of animals are shown in Panel A. Animals were randomized to receive β-CD-3-BrPA (N=21), free 3-BrPA (N=7), gemcitabine (N=7), and β-CD (N=7) Animals were imaged once per week over the course of 28 days. The overall progress of the signal is demonstrated in Panel B. According to Kaplan-Meier analysis, animals treated with free 3-BrPA showed excessive treatment-related toxicity leading to the loss of 5/7 animals at the end of the experiment, such that a statistically relevant number did not survive to be included in the final image analysis (Panel C). The vehicle-control (β-CD) did not demonstrate any treatment-related toxicity and was inert when given intraperitoneally (Panel C). Upon completion of the experiments, all animals were sacrificed and exploratory necropsies were performed in order to extract organs and to assess potential damage. No organ toxicity (tissue effects) was observed for β-CD-3-BrPA, when compared with the inert vehicle (Panel D).
Figure 12:
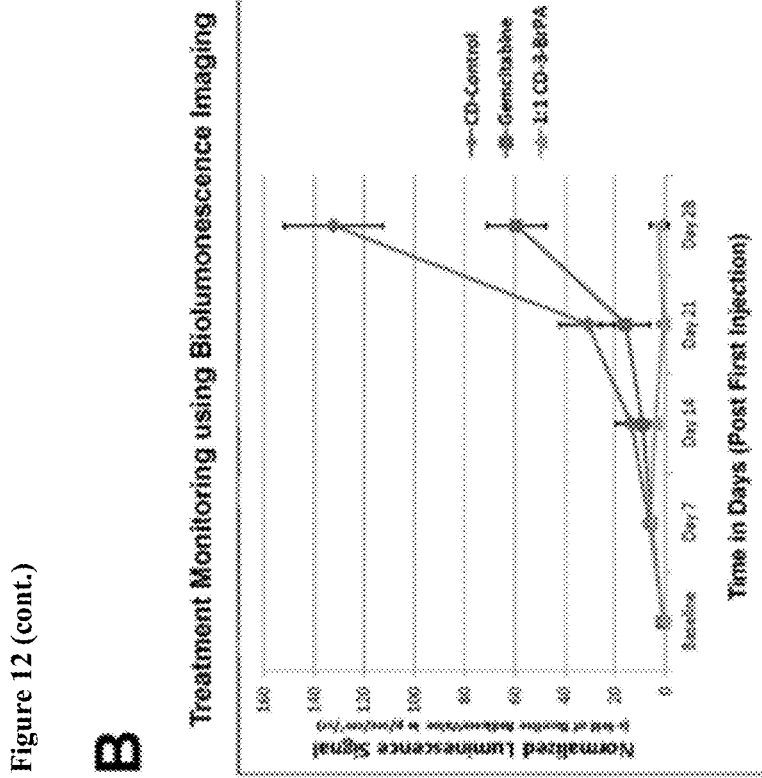
Figure 12:
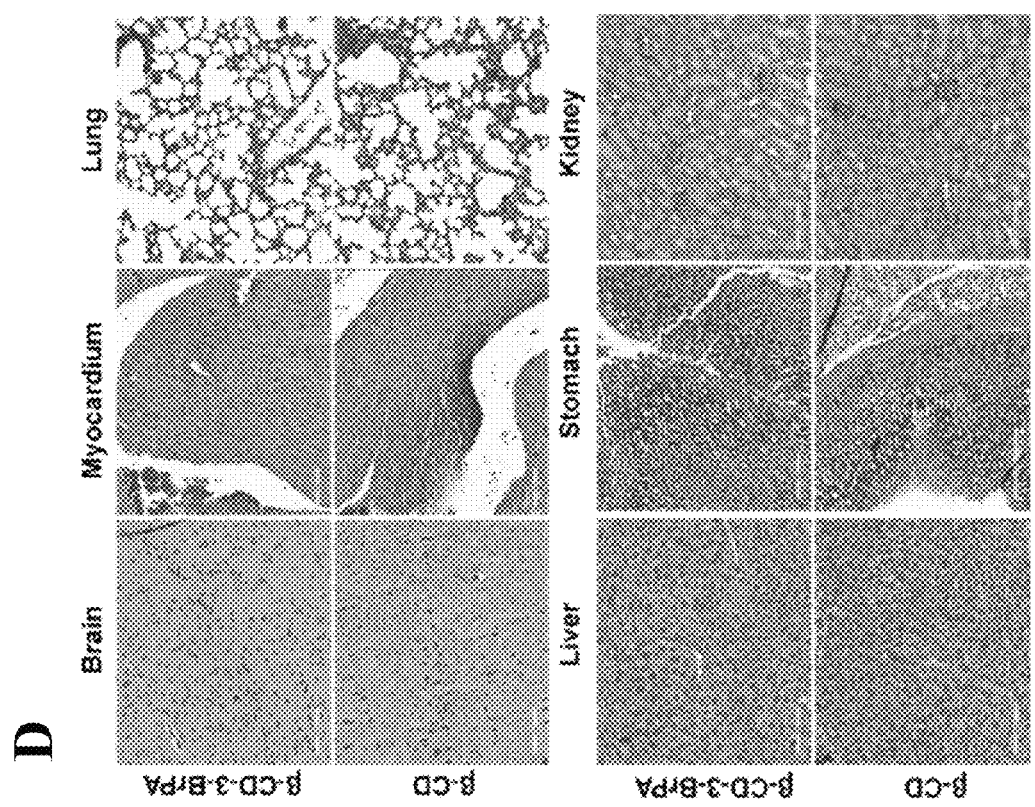
Figure 13:
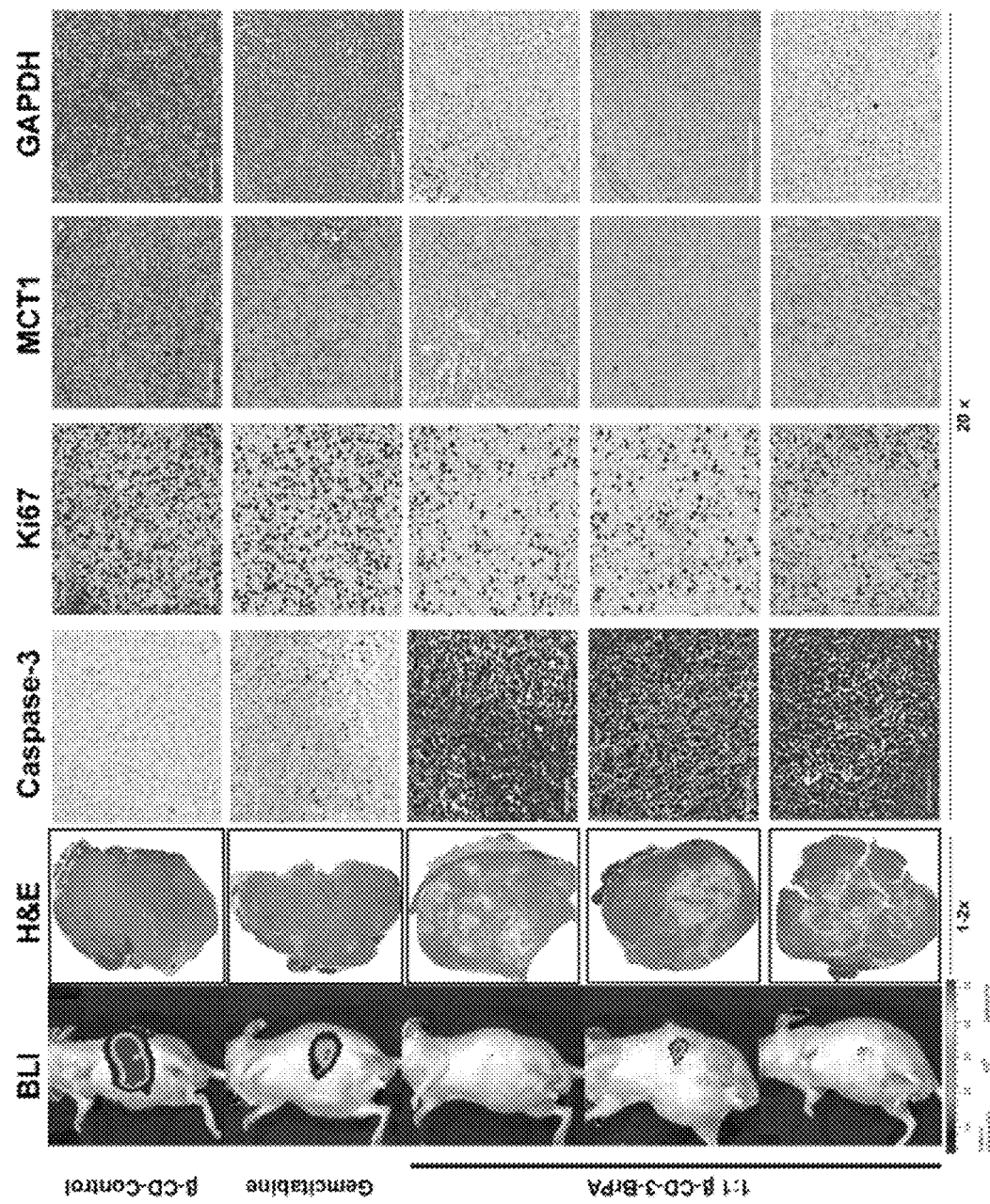
FIG. 13 shows ex vivo pathological and immunohistochemical tumor analysis. The H&E staining of tumors treated with β-CD, gemcitabine, or β-CD-3-BrPA (3 representative tumors are shown) demonstrated the treatment effects of β-CD-3-BrPA. The squares within the H&E-stained whole-tumor overviews indicate the areas magnified for further analysis of the anti-tumoral effects of the drugs, which was confirmed by the staining for cleaved caspase-3 and Ki67. In addition, the marked reduction of GAPDH as the primary target of 3-BrPA, as well as MCT-1 as the specific transporter, was determined.

Example 6: Systemic Delivery of β-CD-3-BrPA Achieves Strong Anti-Cancer Effects In Vivo The anti-cancer efficacy of systemically delivered β-CD-3-BrPA was tested using a xenograft model of human pancreatic cancer in athymic nude mice. Prior to choosing the therapeutic dose for more detailed studies, comparative dose escalation studies in non-tumor-bearing animals were performed for both β-CD-3-BrPA and free 3-BrPA. Accordingly, 20 mg/kg of β-CD-3-BrPA and 10 mg/kg free 3-BrPA were identified as the median lethal doses ($LD_{50}$) after a single injection and 5 mg/kg β-CD-3-BrPA was identified as a safe dose that did not cause any toxicity when given systemically and daily over the course of 7 days. A total of 42 animals with orthotopically-implanted and BLI- and USI-confirmed MiaPaCa-2 tumors were then randomized to receive intraperitoneal (i.p.) injections of β-CD-3-BrPA (N=21), gemcitabine (N=7), or β-CD (N=7). An additional group of animals with orthotopic implants (N=7) was treated with free 3-BrPA. Animals treated with daily intraperitoneal (i.p.) injections of free 3-BrPA (5 mg/kg in 500 µl saline) demonstrated high treatment-related toxicity and 3/7 (43%) animals died before the acquisition of the first follow-up BLI (FIG. 12, Panel C). At the end of the experiment (Day 28), only 2/7 animals (28%) treated with the free drug were still alive (FIG. 12, Panel C). No such mortality rate was observed for any of the remaining groups. Daily i.p. injections of β-CD-3-BrPA (5 mg/kg in 500 µl saline) demonstrated strong anti-cancer effects with early effects visible on day 14 after the first injection (FIG. 12, Panel B). After four weeks of treatment, a comparison of BLI signal intensity between the groups was performed. Animals treated with the β-CD control demonstrated a 140-fold signal increase as compared to baseline. A moderate deceleration of tumor growth was observed in gemcitabine-treated animals with a 60-fold signal increase over time. Most importantly, animals treated with β-CD-3-BrPA showed minimal or no progression of the signal as compared to gemcitabine and control groups (FIG. 12). After achieving this endpoint, animals were sacrificed and tumors were harvested for further analysis. All animals were subjected to necropsies and organs (brain, heart, lungs, bowel, liver, and kidneys) were harvested for the analysis of potential tissue damage. No organ toxicities or tissue damage was observed in animals treated with β-CD-3-BrPA (FIG. 12, Panel D). The analysis of tumor pathology demonstrated vast tumor destruction with central areas of colliquative necrosis in animals treated with β-CD-3-BrPA (FIG. 13). Tumor regions with intact cell junctions demonstrated a high expression of cleaved caspase-3, indicating fulminant tumor apoptosis. Animals treated with β-CD-3-BrPA demonstrated a significant reduction in proliferation as assessed with Ki67 immunohistochemistry with a mean of 17% and 51%, respectively (FIG. 13). In addition, animals treated with β-CD-3-BrPA demonstrated lower expression levels of MCT1 and GAPDH within the treated tumors as compared to the β-CD or gemcitabine groups.

These results indicate that systemically delivered β-CD-3-BrPA achieved strong anti-tumoral effects in vivo while causing much less toxicity in therapeutic doses when compared to the free drug. Furthermore, microencapsulation of 3-BrPA did not alter the efficacy of the drug against pancreatic cancer cells in vitro, which was demonstrated using 2D, as well as ECM-rich 3D cell cultures, both under normoxic and hypoxic conditions. The abilities of 3-BrPA to inhibit the secretion of MMP-9 and to reduce the invasiveness of pancreatic cancer cells in sublethal doses further indicates the anti-metastatic potential of this drug.

Selectively targeting tumor metabolism has long been considered as a desirable therapeutic option, but has yet not been translated into clinical practice. The primary limitation in reaching the milestone of systemic deliverability with 3-BrPA is the reported toxicity due to its alkylating properties (Ganapathy-Kanniappan and Geschwind (2013) Mol. Cancer 12:152; Chang et al. (2007) Acad. Radiol. 14:85-92; Kunjithapatham et al. (2013) BMC Res. Not. 6:277). As a result, local image-guided delivery of the drug has been explored as an alternative therapeutic option; however, the practical use of these approaches is limited to treating localized disease (Ota et al. (2013) Target. Oncol. 8:145-151; Geschwind et al. (2002) Canc. Res. 62:3909-3913). The results described herein clearly demonstrate that the drug, when appropriately formulated for systemic delivery, was extremely effective, thereby expanding the use of this compound to virtually any cancer. These results contrast to those of the only other study where the drug was used systemically in its free form to treat solid tumors. In that study, free 3-BrPA failed to elicit any meaningful tumor response at the dose used in the experiments described herein (Cao et al. (2008) Clin. Canc. Res. 14:1831-1839; Schaefer et al. (2012) Translat. Res. 159:51-57). Specifically, a study, which explored the systemic delivery of free 3-BrPA in combination with an HSP90 inhibitor in subcutaneous pancreatic cancer xenografts, did not report any significant efficacy for 3-BrPA alone in a dose of 5 mg/kg, given twice per week out of safety considerations (Cao et al. (2008) Clin. Canc. Res. 14:1831-1839). A possible explanation for this unfavorable efficacy profile of the free drug is the rapid inactivation of 3-BrPA through unspecific interaction with serum proteins, which is known to occur in vivo as early as 2-3 minutes after systemic administration (Kunjithapatham et al. (2013) BMC Res. Not. 6:277). Some efficacy was observed at these doses, but excessive toxicity, with treatment-related deaths in most animals, was the predominant result. Hence, it is believed that systemic administration of free 3-BrPA may not be effective and may promote undesirable toxicities. It is also believed that in the microencapsulated formulation, 3-BrPA is more bioavailable for uptake into tumor cells and less available to the normal cells that apparently mediate its toxicity (Birsoy et al. (2013) Nature Genet. 45:104-108; Zhang and Ma (2013) Advanc. Drug Deliv. Rev. 65:1215-1233; Heidel and Schluep (2012) J. Drug Deliv. 2012:262731).

A characteristic feature of pancreatic tumor tissue is the excessive accumulation of dense ECM which limits oxygen diffusion and creates a highly hypoxic, ill-perfused tumor microenvironment known for its profound chemoresistance and increased invasiveness (Yokoi and Fidler (2004) Clin. Canc. Res. 10:2299-2306; Yang et al. (2001) J. Surg. Res. 98:33-39). Published studies confirmed that more than 30% of pancreatic tumor cells are located in hypoxic tumor compartments, thereby escaping the effects of conventional chemotherapy. These cells then go on to re-form a tumor that has become even more aggressive and resistant to chemotherapy (Guillaumond et al. (2013) Proc. Natl. Acad. Sci. U.S.A. 110:3919-3924). The results described herein demonstrate that 3-BrPA is able to effectively block tumor glycolysis even when it is exacerbated under hypoxic conditions. On the contrary, the inability of gemcitabine, even at the highest dose, to cope with hypoxia in pancreatic cancer cells was confirmed. So far, conflicting data have been reported for the oxygen dependency of 3-BrPA in cancer cells (Cao et al. (2008) Canc. Chemother. Pharmacol. 62:985-994; Xiao et al. (2013) Oncol. Rep. 29:329-334). However, there is significant evidence in support of the ability of 3-BrPA to overcome hypoxia as a key mechanism of drug resistance (Xu et al. (2005) Canc. Res. 65:613-621). Specifically, more recent studies established the link between hypoxia and the expression of MCT-1, which was shown to be overexpressed in hypoxic cells and tumor regions, thus providing the functional explanation for as the increased sensitivity of hypoxic tumor tissue towards 3-BrPA (Matsumoto et al. (2013) Magnet. Res. Med. 69:1443-1450). Of note, combining gemcitabine and 3-BrPA in order to potentially achieve an increase of efficacy has been explored in vitro; however, no combination effects were identified and, accordingly, no respective in vivo experiments were performed.

Furthermore, the use of the collagen 1-rich 3D organotypic cell culture as a model for an ECM-rich tumor microenvironment has demonstrated the ability of 3-BrPA to successfully penetrate the matrix without any measurable reduction of efficacy as compared to the monolayer cell culture. The 3D cell culture model used in the studies described herein can be seen as relatively specific primarily because it is composed of a matrix, which mimics the collagen 1-rich ECM as seen in in human ex vivo samples (Mollenhauer et al. (1987) Pancreas 2:14-24). While the benefits of such in vitro models for the purpose of drug testing are increasingly recognized, mimicking these conditions in vivo represents a greater challenge (Longati et al. (2013) BMC Canc. 13:95). When designing this study, different animal models were considered. On the one hand, using a widely recognized orthotopic xenograft model brings about important advantages, such as reproducibility, predictable tumor growth dynamics, as well as allowing for genomic modification of tumor cells to express specific and imageable reporter genes (Kim et al. (2009) Nat. Protocol. 4:1670-1680). On the other hand, the degree to which these models reflect the tumor microenvironment in human lesions remains unknown. Although several well defined mouse tumor models are able to mimic the ECM-component and tumor hypoxia more realistically, these models seem as less suitable for the purpose of standardized drug testing (Guillaumond et al. (2013) Proc. Natl. Acad. Sci. U.S.A. 110:3919-3924). In light of the demonstrated ability of 3-BrPA to inhibit cell invasiveness in vitro, the use of a metastatic Suit-2 xenograft model was considered. However, orthotopic implantation of Suit-2 xenografts resulted in complications (i.e., bloody ascites) and loss of a majority of animals within 14 days after implantation, which facilitated the selection of MiaPaCa-2 xenografts as a practicable alternative.

An additional unexpected result was observed in the immunohistochemical analysis of treated tumor tissues: next to the anticipated and previously reported depletion of GAPDH as the molecular target of 3-BrPA, the amount of MCT-1 as the specific transporter for 3-BrPA was significantly reduced in treated samples (Ganapathy-Kanniappan et al. (2012) *Radiol.* 262:834-845). No evidence has heretofore existed for the presence of MCT-1 as a potential target of 3-BrPA. Yet, this lactate transporter has been repeatedly identified as a suitable molecular target of cancer therapy (Schneiderhan et al. (2009) *Gut* 58:1391-1398; Shih et al. (2012) *Oncotarget* 3:1401-1415; Sonveaux et al. (2012) *PloS One* 7:e33418).

Thus, the results described herein identified microencapsulation of 3-BrPA as a promising advance towards finally achieving the goal of systemically deliverable anti-glycolytic tumor therapy. The strong anti-cancer effects of β-CD-3-BrPA and the favorable toxicity profile pave the way towards clinical trials in patients with pancreatic cancer and potentially other malignancies.

INCORPORATION BY REFERENCE

The contents of all references, patent applications, patents, and published patent applications, as well as the Figures and the Sequence Listing, cited throughout this application are hereby incorporated by reference. It will be understood that, although a number of patent applications, patents, and other references are referred to herein, such reference does not constitute an admission that any of these documents forms part of the common general knowledge in the art.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A composition comprising a β-cyclodextrin and a pharmaceutical agent, wherein the pharmaceutical agent is a 3-halopyruvate, wherein at least one α-D-glucopyranoside unit of the cyclodextrin has at least one hydroxyl chemical group replaced with an ionizable chemical group resulting in a negative charge and
wherein the cyclodextrin encapsulates the pharmaceutical agent.

2. The composition of claim 1, wherein the at least one hydroxyl chemical group of the at least one α-D-glucopyranoside unit is selected from the group consisting of C2, C3, and C6 hydroxyl chemical groups.

3. The composition of claim 2, wherein the C2, C3, and C6 hydroxyl chemical groups of at least one α-D-glucopyranoside unit of the cyclodextrin are replaced with ionizable chemical groups.

4. The composition of claim 1, wherein the at least one α-D-glucopyranoside unit of the cyclodextrin is selected from the group consisting of two, three, four, five, six, seven, eight, and all α-D-glucopyranoside units of the cyclodextrin.

5. The composition of claim 1, wherein the ionizable chemical group is the same at all replaced positions.

6. The composition of claim 1, wherein the ionizable chemical group is a weakly basic functional group or a weakly acidic functional group.

7. The composition of claim 6, wherein the weakly basic functional group (X) has a $pK_a$ between 6.5 and 8.5 according to CH3-X$^-$.

8. The composition of claim 6, wherein the weakly acidic functional group (Y) has a $pK_a$ between 4.0 and 6.5 according to $CH_3$—Y.

9. The composition of claim 6, wherein the weakly basic or weakly acidic functional groups are selected from the group consisting of amino, ethylene diamino, dimethyl ethylene diamino, dimethyl anilino, dimethyl naphthylamino, succinyl, carboxyl, sulfonyl, and sulphate functional groups.

10. The composition of claim 1, wherein the cyclodextrin has a $pK_{a1}$ of between 4.0 and 8.5.

11. The composition of claim 1, wherein the composition is a liquid or solid pharmaceutical formulation.

12. The composition of claim 1, wherein the pharmaceutical agent is neutrally charged or hydrophobic.

13. The composition of claim 1, wherein the β-cyclodextrin is selected from the group consisting of 6' modified β-cyclodextrin, 6' mono-succinyl β-cyclodextrin, hydroxypropyl-β-cyclodextrin, and succinyl-β-cyclodextrin.

14. The composition of claim 1, wherein the pharmaceutical agent is 3-bromopyruvate.

15. The composition of claim 1, wherein the composition is formulated for systemic administration.

16. The composition of claim 1, further comprising an anti-cancer therapeutic agent.

17. A kit comprising a composition of claim 1, and instructions for use.

18. A method of treating a subject having a cancer comprising administering to the subject a therapeutically effective amount of a composition of claim 1.

19. The method of claim 18, wherein the composition is administered systemically.

20. The method of claim 19, wherein the systemic administration is selected from the group consisting of oral, intravenous, intraperitoneal, subcutaneous, and intramuscular administration.

21. The method of claim 18, wherein the subject is treated with at least one additional anti-cancer therapy.

22. The method of claim 21, wherein the at least one additional anti-cancer therapy is radiation therapy.

23. The method of claim 18, wherein the cancer is a solid tumor.

24. The method of claim 18, wherein the cancer is selected from the group consisting of liver cancer, pancreatic cancer, lung cancer and breast cancer.

25. The method of claim 24, wherein the cancer is liver cancer.

26. The method of claim 18, wherein the subject is a mammal.

27. The method of claim 26, wherein the mammal is a human.

* * * * *